(12) United States Patent
Sugizaki

(10) Patent No.: US 11,834,700 B2
(45) Date of Patent: Dec. 5, 2023

(54) METHOD FOR ANALYZING TARGET PARTICLE, ANALYTICAL REAGENT, AND ANALYZER

(71) Applicant: KABUSHIKI KAISHA TOSHIBA, Tokyo (JP)

(72) Inventor: Yoshiaki Sugizaki, Fujisawa Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 36 days.

(21) Appl. No.: 17/447,469

(22) Filed: Sep. 13, 2021

(65) Prior Publication Data

US 2022/0298544 A1   Sep. 22, 2022

(30) Foreign Application Priority Data

Mar. 19, 2021   (JP) ................. 2021-045863

(51) Int. Cl.
| | |
|---|---|
| *C12Q 1/68* | (2018.01) |
| *C12Q 1/6806* | (2018.01) |
| *G01N 33/543* | (2006.01) |
| *C12N 9/22* | (2006.01) |

(52) U.S. Cl.
CPC ............ *C12Q 1/6806* (2013.01); *C12N 9/22* (2013.01); *G01N 33/54326* (2013.01)

(58) Field of Classification Search
None
See application file for complete search history.

(56) References Cited

U.S. PATENT DOCUMENTS

2020/0087707 A1* 3/2020 Engreitz ............. C12Q 1/6806

FOREIGN PATENT DOCUMENTS

JP   2020-46284 A   3/2020

OTHER PUBLICATIONS

Hansen et al., 2014, Biio Techniques, 56:217-228 (Year: 2014).*
A. Hoshino, et al., "Tumour exosome integrins determine organotropic metastasis," Nature, vol. 527, No. 7578, pp. 329-335 (19 pages) (2015).
Y. Yang, et al., "Interferometric plasmonic imaging and detection of single exosomes," Proc. of the Nat'l Academy of Sciences, vol. 115, No. 41, p. 10275-280 (2018).

* cited by examiner

*Primary Examiner* — Jehanne S Sitton
(74) *Attorney, Agent, or Firm* — Finnegan, Henderson, Farabow, Garrett & Dunner, LLP

(57) ABSTRACT

According to one embodiment, a method includes dispensing the specimen into $first_1$ to $first_n$ containers configured to capture the target particle, removing a contaminant other than the target particle to be captured from the specimen, adding first to m-th probes to the $first_1$ to $first_n$ containers, removing excessive first to m-th probes that have not bound to the target particle, individually amplifying the reporter portion for each of the $first_1$ to $first_n$ containers using the common primer set to obtain first to n-th amplification products, removing an excessive common primer set from the first to n-th amplification products, dispensing the first to n-th amplification products into $second_1$ to $second_m$ containers respectively, amplifying the amplification products in the $second_1$ to $second_m$ containers using the first to m-th specific primer sets, and analyzing presence or absence or types of the target particles captured in the $first_1$ to $first_n$ containers.

18 Claims, 18 Drawing Sheets

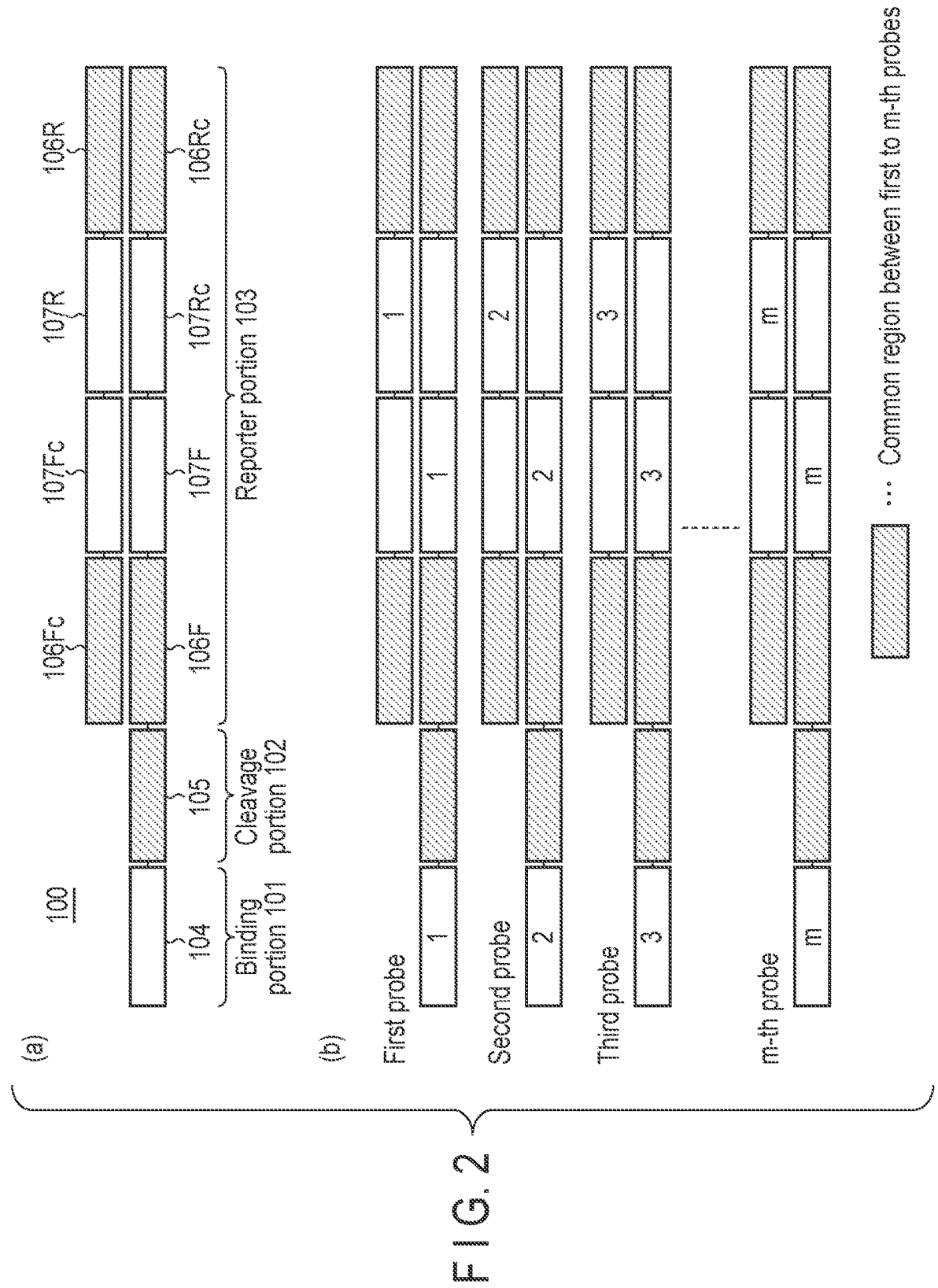
F I G. 2

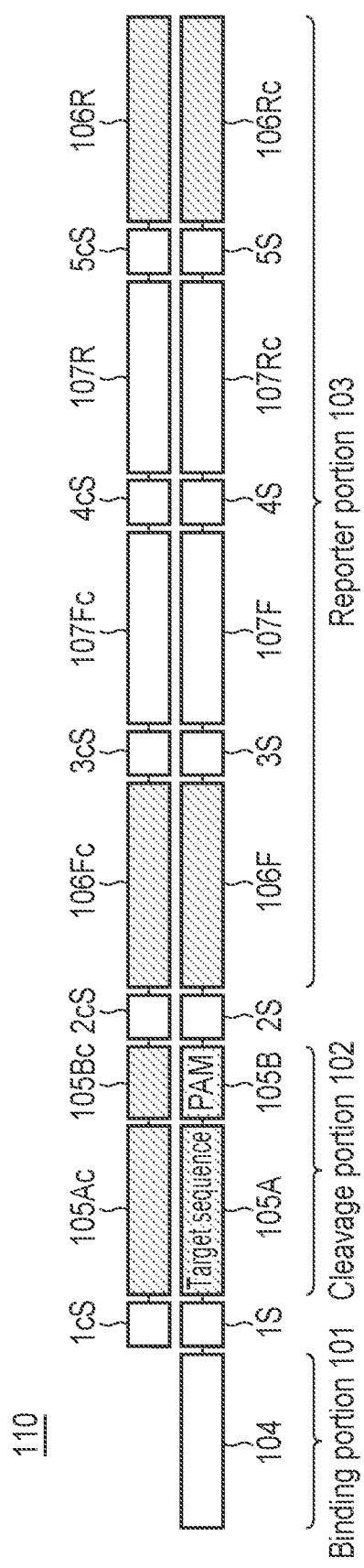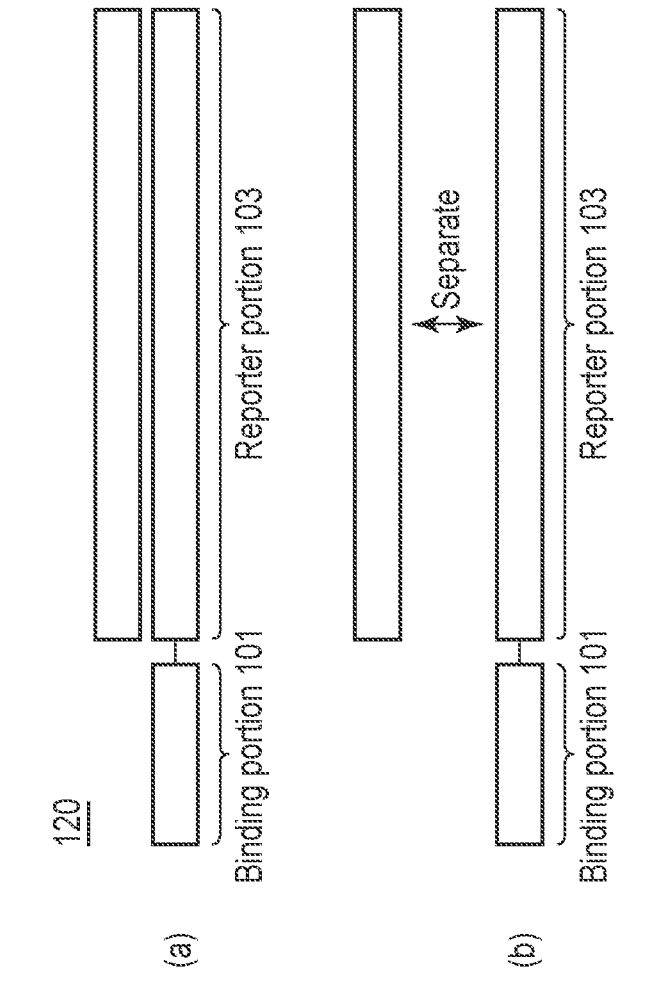

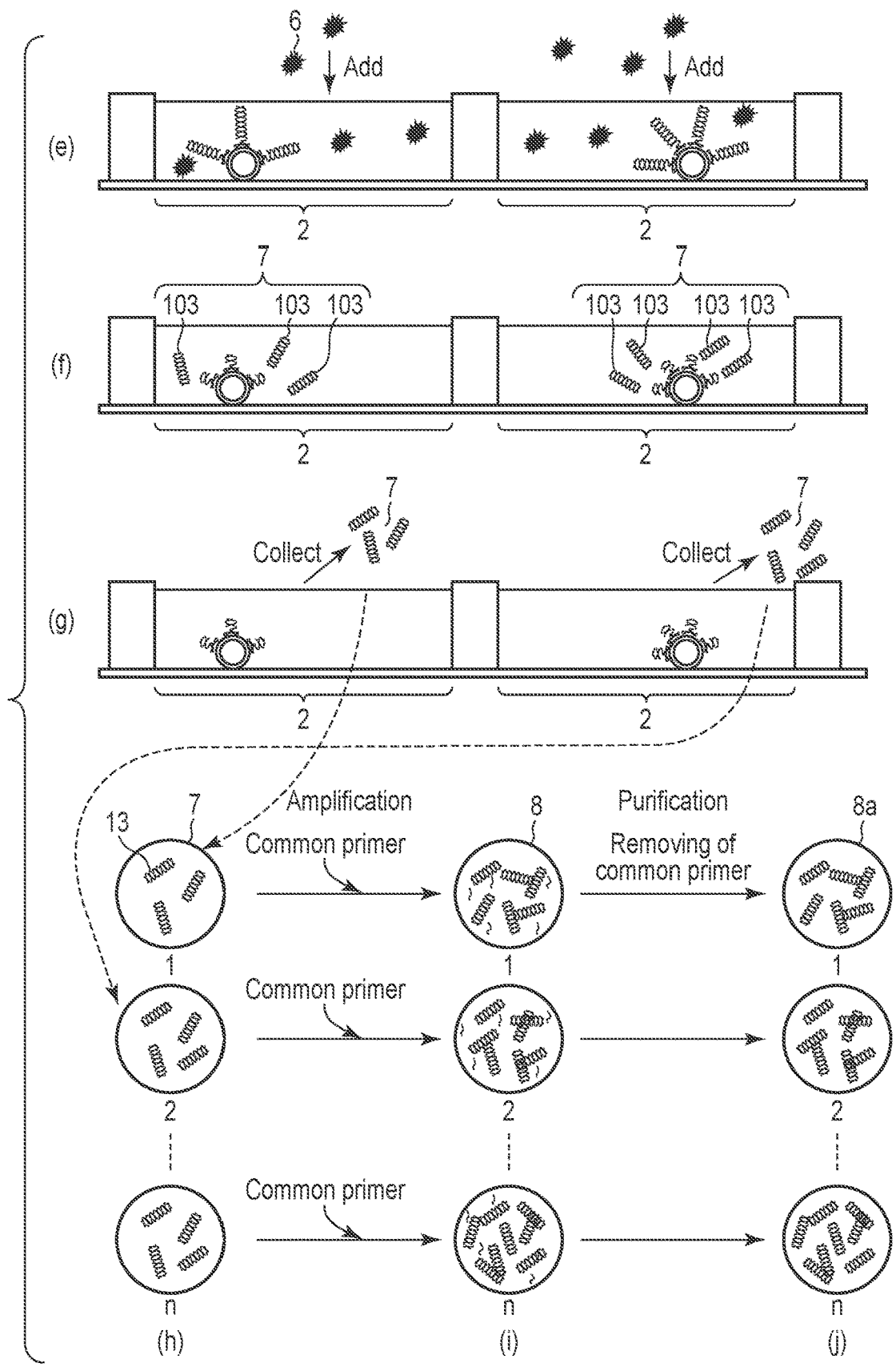
F I G. 10

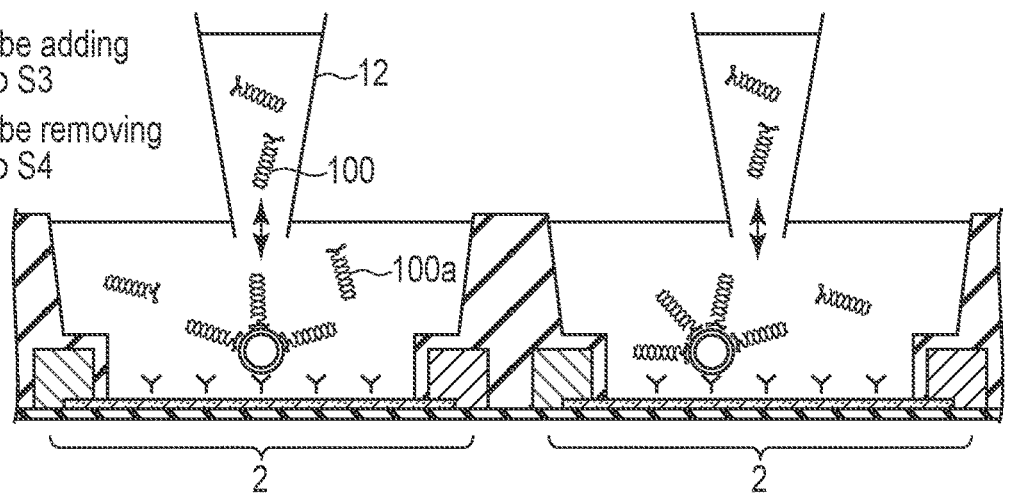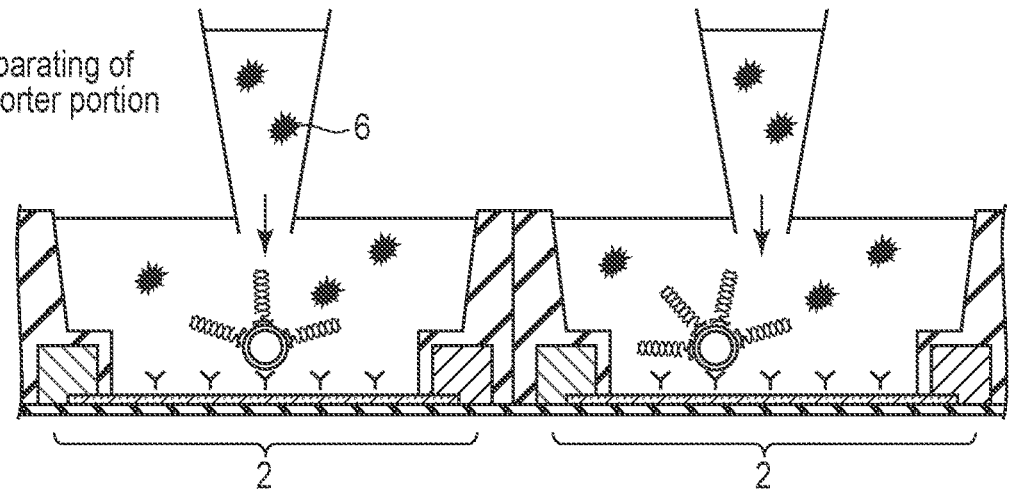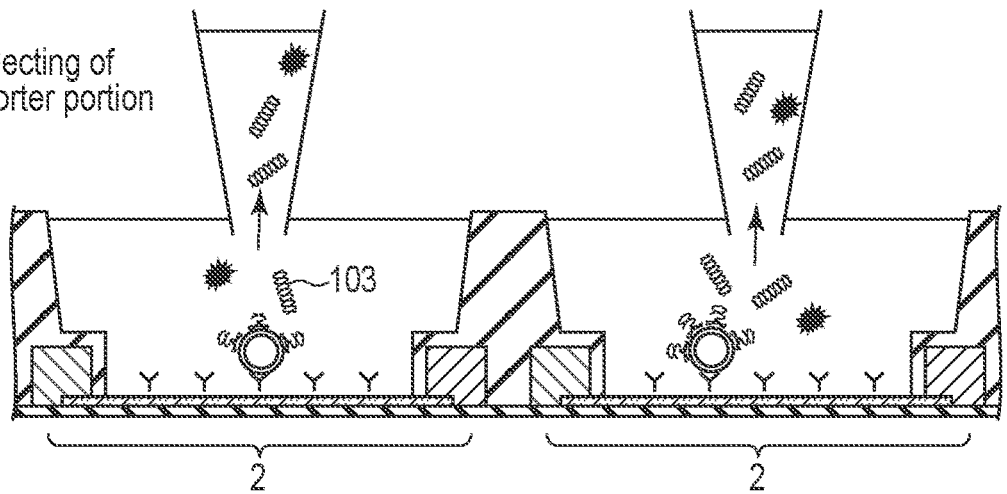
FIG. 15

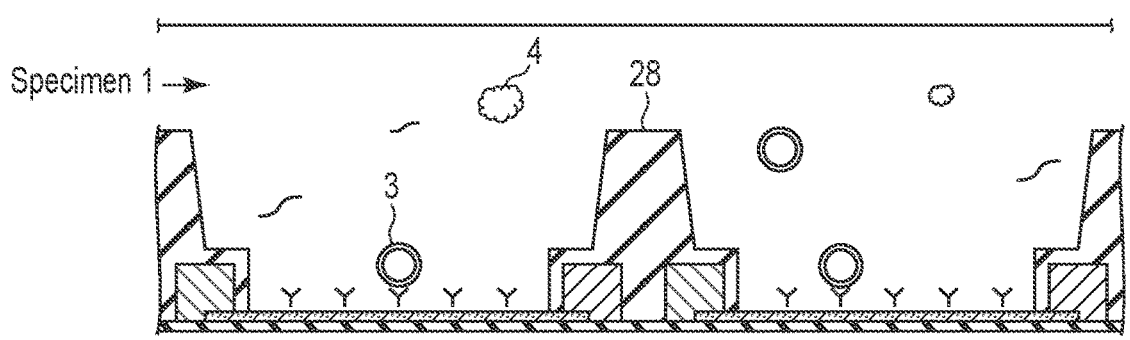
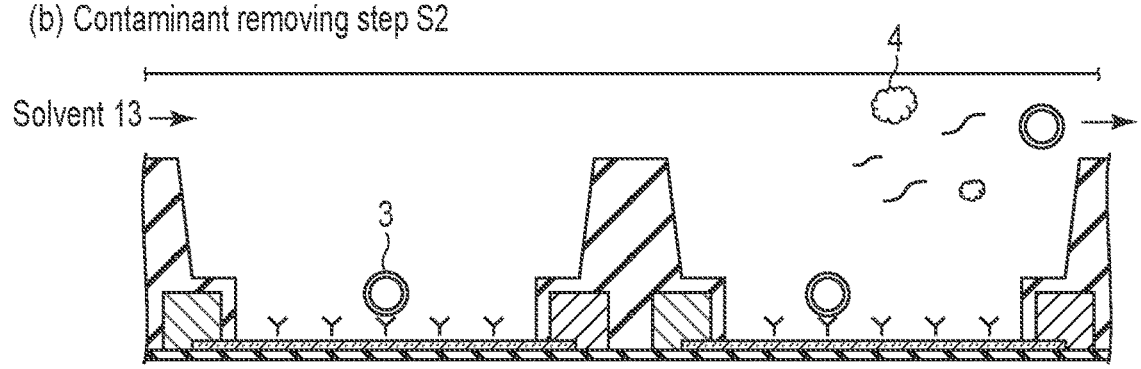
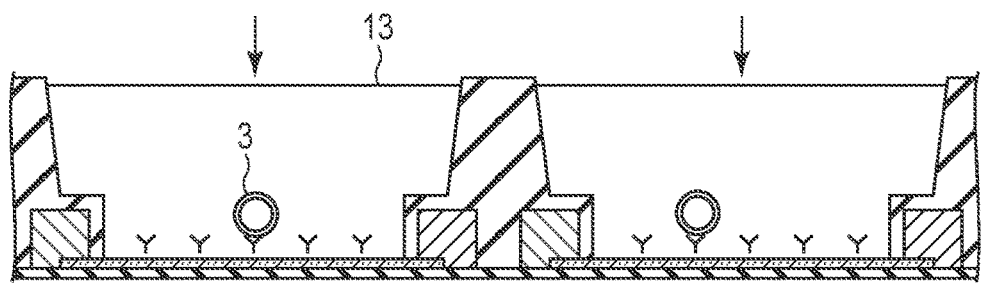
FIG. 16

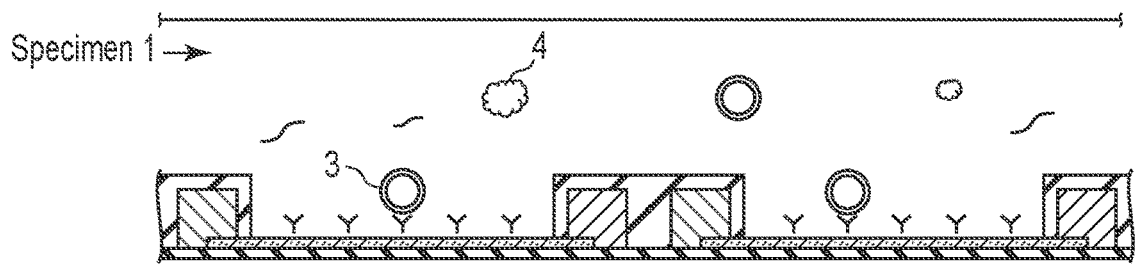
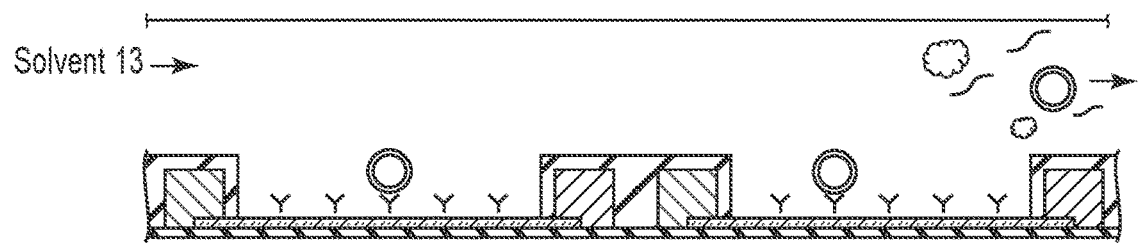
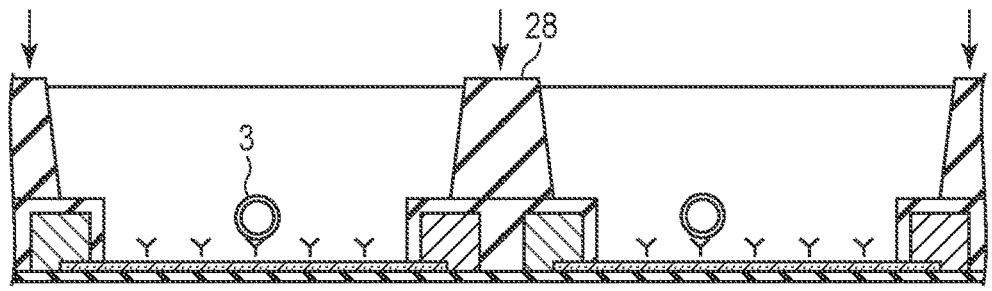
FIG. 17

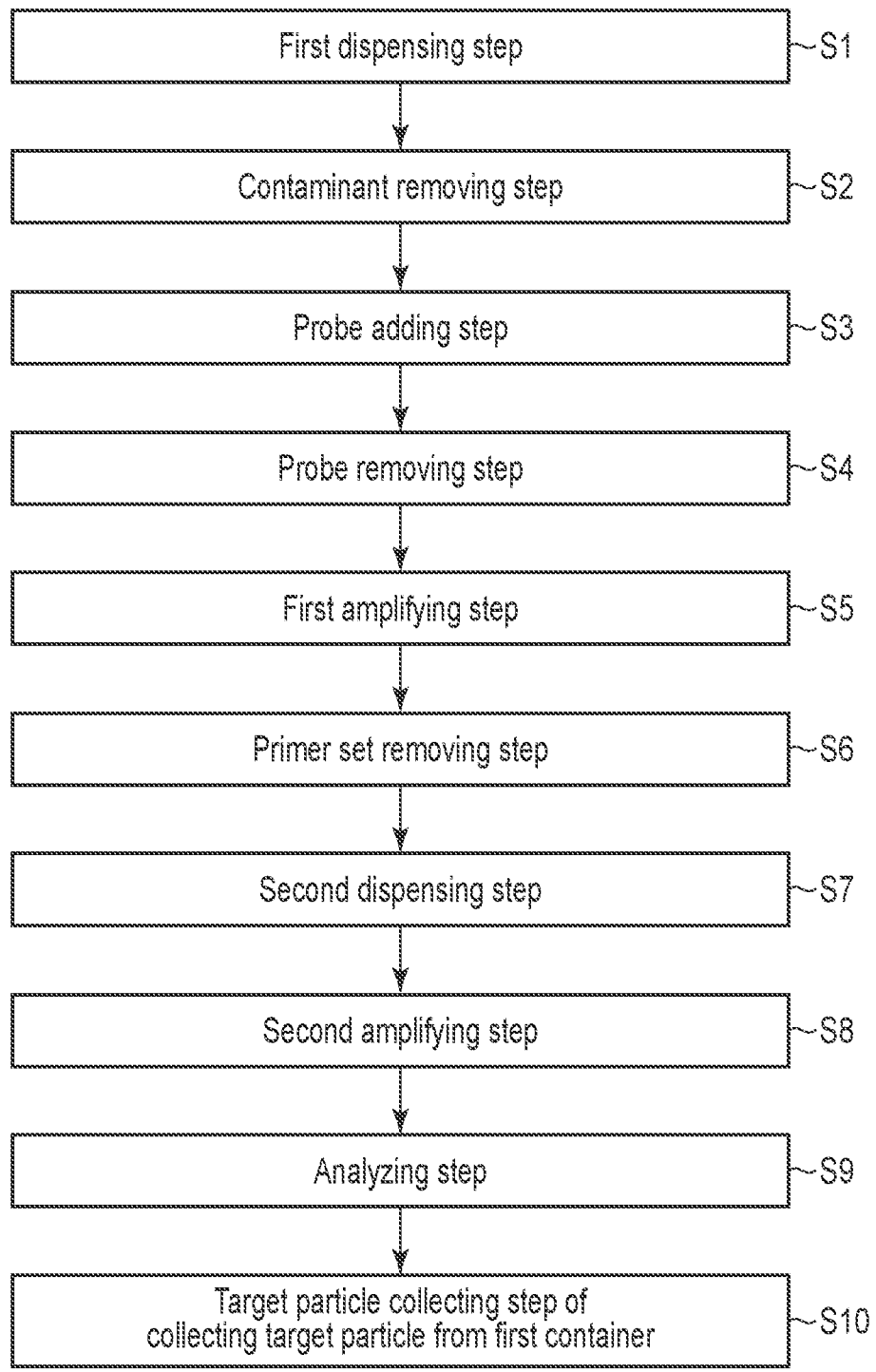
F I G. 18

METHOD FOR ANALYZING TARGET PARTICLE, ANALYTICAL REAGENT, AND ANALYZER

CROSS-REFERENCE TO RELATED APPLICATIONS

This application is based upon and claims the benefit of priority from Japanese Patent Application No. 2021-045863, filed on Mar. 19, 2021, the entire contents of which are incorporated herein by reference.

FIELD

Embodiments described herein relate generally to a method for analyzing a target particle, an analytical reagent, and an analyzer.

BACKGROUND

Extracellular vesicles are minute vesicles with a particle size of around 100 nm contained in a living body. It has been known that extracellular vesicles have a lipid bilayer membrane structure containing nucleic acids and the like therein, move between distant organs, and have a function of transporting substances and transmitting information. Observation results suggesting that the lipid bilayer membrane contains protein, glycoprotein, or the like, and cfDNA is attached around the lipid bilayer membrane have also been reported. It is considered that the results include information on cells (donor cells) in which extracellular vesicles are produced, information on cells (recipient cells) at a transmission destination, and the like.

The extracellular vesicles have been reported to be deeply involved in cancer metastasis. Alternatively, it has been reported that it is involved in the transport of causative substances in diseases other than cancer, such as Alzheimer's disease, Parkinson's disease, dementia with Lewy bodies, neurodegenerative diseases, and renal disorders. Therefore, the extracellular vesicles have attracted attention as biomarkers for use in disease detection, recurrence monitoring, and the like. In addition, since there are many unclear points in terms of the configuration and function thereof, it has attracted attention as a research object, and development of a method for analyzing extracellular vesicles has been desired.

BRIEF DESCRIPTION OF THE DRAWINGS

FIG. 2 is a diagram illustrating an example of a probe according to the embodiment.

FIG. 6 is a diagram illustrating an example of the probe according to the embodiment.

FIG. 7 is a diagram illustrating an example of the probe according to the embodiment.

FIG. 10 is a diagram illustrating an example of procedures of separation and collection of the reporter portion and amplification of the reporter portion in the analysis method of the embodiment.

FIG. 15 is a diagram illustrating an example of a procedure of the analysis method of the embodiment.

FIG. 16 is a diagram illustrating an example of a procedure of the analysis method of the embodiment.

FIG. 17 is a diagram illustrating an example of a procedure of the analysis method of the embodiment.

FIG. 18 is a flowchart illustrating an example of the analysis method according to the embodiment.

DETAILED DESCRIPTION

Figure 1:
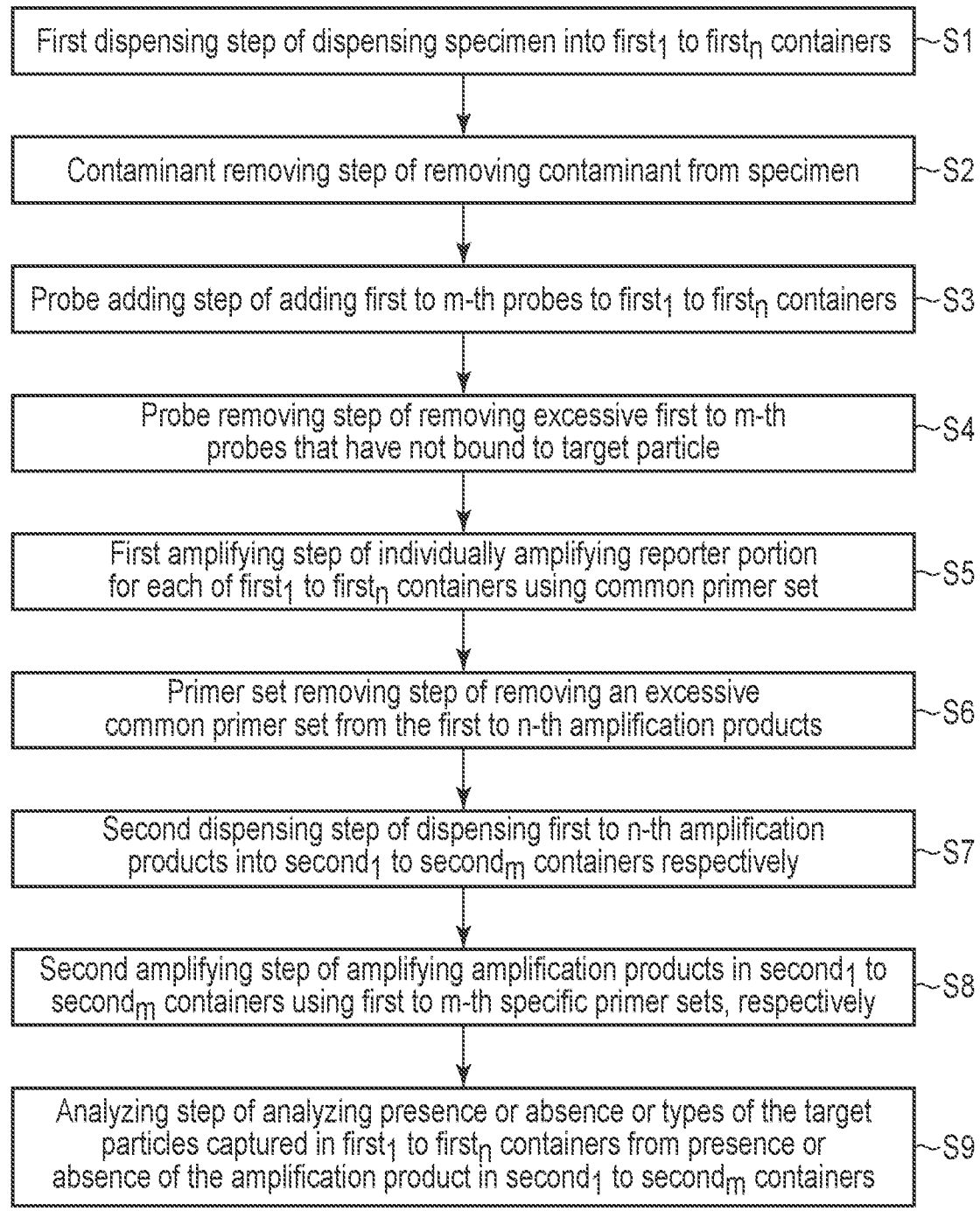
FIG. 1 is a flowchart illustrating an example of an analysis method according to an embodiment.

In general, according to one embodiment, a problem to be solved by the invention is providing a method, an analytical regent, and an analyzer capable of comprehensively analyzing a target particle in a specimen at a time.

An analysis method according to one embodiment is a method to analyze a target particle in a specimen. The method comprises dispensing the specimen into $first_1$ to $first_n$ containers configured to capture the target particle, removing a contaminant other than the target particle to be captured from the specimen, adding first to m-th probes to the first1 to $first_n$ containers, the first to m-th probes having at least a binding portion that specifically binds to any one of first to m-th surface markers of the target particle and a nucleic acid reporter portion including a common amplification sequence to which a common primer set binds and a specific amplification sequence to which a specific primer set binds and which is disposed in a region amplified by the common amplification sequence, in which the binding portion and the specific amplification sequence are different from each other between the first to m-th probes, removing excessive first to m-th probes that have not bound to the target particle, individually amplifying the reporter portion for each of the $first_1$ to $first_n$ containers using the common primer set to obtain first to n-th amplification products, removing an excessive common primer set from the first to n-th amplification products, and dispensing the first to n-th amplification products into $second_1$ to $second_m$ containers respectively, further amplifying the amplification products in the second1 to $second_m$ containers using the first to m-th specific primer sets, respectively, and analyzing presence or absence or types of the target particles captured in the $first_1$ to $first_n$ containers by determining the types of surface markers present in the $first_1$ to $first_n$ containers from the presence or absence of the amplification product by the specific primer set in the second$_1$ to second$_m$ containers, wherein the n and m are integers of 2 or more.

Hereinafter, embodiments will be described with reference to the accompanying drawings. Note that, in each embodiment, substantially the same constituent parts are denoted by the same reference signs and an explanation thereof will be partly omitted in some cases. The drawings are schematic, and a relation of thickness and planer dimension of each part, an analysis method, thickness ratio among parts, and so on are sometimes different from actual ones.

Analysis Method

An analysis method according to an embodiment is a method for analyzing a target particle in a specimen.

The target particle is a minute vesicle surrounded by a membrane such as a lipid bilayer membrane and having a structure containing various substances inside. The target particle is, for example, a biological vesicle having a diameter of about 20 to 500 nm, and may be, for example, an extracellular vesicle such as an exosome, a microvesicle, or an apoptotic endoplasmic reticulum, a virus, or the like.

The specimen is a liquid that can contain a target particle. The specimen is, for example, of biological origin, and is blood, serum, plasma, blood cells, urine, feces, sweat, saliva, sputum, lymph, cerebrospinal fluid, lacrimal fluid, breast milk, amniotic fluid, semen, a cell extract, a tissue extract, a mixture thereof, or the like. Alternatively, the specimen may be a material derived from a plant such as sap or fruit juice, or may be a sample derived from an environment such as soil, river water, sea water, or a mixture thereof.

The present analysis method can simultaneously and comprehensively analyze the type, amount, concentration, and/or the like of a plurality of target particles that can be contained in a specimen. It is done by detection of specific surface markers that may be present on the surface of the target particle.

In performing the analysis method, first, a target surface marker to be analyzed is determined. The surface marker may be, for example, a protein, a glycoprotein, a lipid, a sugar chain, or cfDNA attached to the surface of the target particle. For example, a plurality of specific target particles is selected as a target of one analysis, and a target surface marker to be detected by the present analysis method is determined among surface markers of each of the target particles. The target surface marker is preferably one that can specifically identify each target particle by the type or combination thereof. The target particle group selected here may be target particles considered to be related to a specific health condition of an individual from whom a specimen is collected, for example, a disease or an infectious disease. Alternatively, a large number of surface markers of a wide variety of target particles may be analyzed. Examples of the surface marker include, but are not limited to, cluster of differentiation (CD) 9, CD63, CD81, CD82, integrin α6β4, integrin αvβ5, integrin αvβ3, epCAM, hemagglutinin, neuraminidase, and the like.

For example, when four types of target particles A, B, C, and D are to be analyzed, target surface markers a, b, and c are selected for the target particle A, target surface markers a, c, and d are selected for the target particle B, target surface markers b, e, and f are selected for the target particle C, and in a case where target surface markers c and e are selected for the target particle D, the target surface markers are also six types of a, b, c, d, e, and f. For example, a is a first surface marker, b is a second surface marker, c is a third surface marker, d is a fourth surface marker, e is a fifth surface marker, and f is a sixth surface marker.

In addition, an analytical reagent is prepared based on the selected target surface marker. The analytical reagent includes a probe. When the number of target surface markers is m, m types of probes are prepared. m is an integer of 2 or more. In the examples of the target particles A, B, C, and D, first to sixth probes respectively corresponding to the first to sixth surface markers are prepared as indicated in Table 1. The number m of the probes 100 is not limited to 6 as in the example indicated in Table 1, and m is preferably, for example, 3 to 50.

TABLE 1

| Target particle | Target surface marker | | | | | |
| --- | --- | --- | --- | --- | --- | --- |
| | a | b | c | d | e | f |
| A | + | + | + | | | |
| B | + | | + | + | | |
| C | | + | | | + | + |
| D | | | + | | + | |
| Probe | First | Second | Third | Fourth | Fifth | Sixth |

Hereinafter, a configuration of the probe will be described with reference to FIG. 2. As illustrated in part (a) of FIG. 2, the probe 100 includes, for example, a binding portion 101, a cleavage portion 102, and a reporter portion 103.

The binding portion 101 includes a binder 104 that specifically binds to a target surface marker. The binders 104 of the first to m-th probes correspond to the first to m-th surface markers, respectively, and bind to the first to m-th surface markers, respectively. Therefore, as illustrated in part (b) of FIG. 2, the binding portions 101 are different from each other between the first to m-th probes. The binder 104 is an antibody or an antigen-binding fragment, a lectin, a naturally occurring nucleic acid, an artificial nucleic acid, an aptamer, a peptide aptamer, an oligopeptide, a protein, or the like.

As illustrated in part (a) of FIG. 2, the cleavage portion 102 is formed of a body to be cleaved 105. The body to be cleaved 105 is configured to be cut by performing a specific operation such as addition of a cleavage reagent. The cleavage portion 102 is provided to separate the reporter portion 103 from the probe 100 at a specific time point in the present analysis method.

Figure 3:
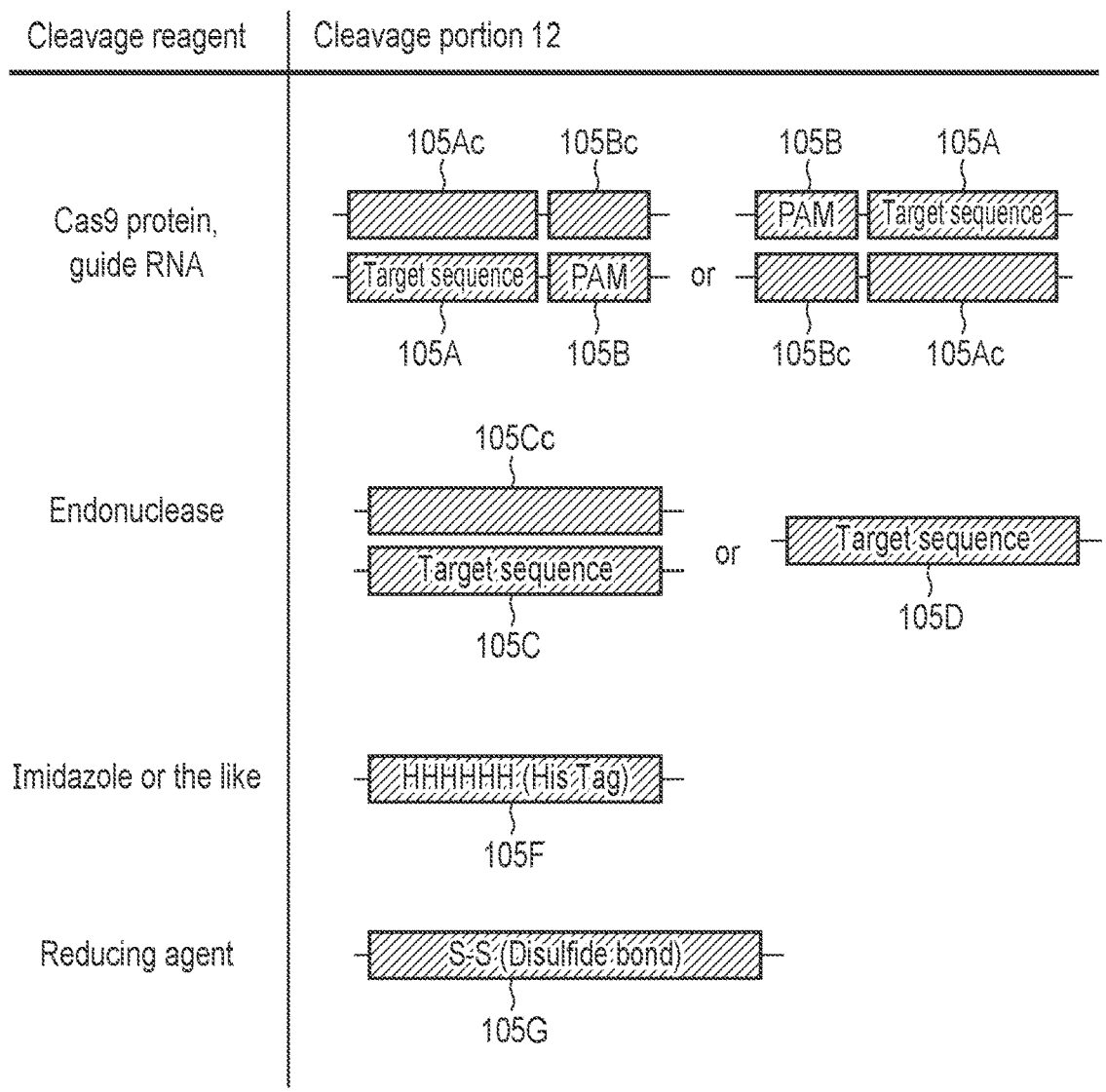
FIG. 3 is a diagram illustrating an example of a cleavage portion and a cleavage reagent of the embodiment.

FIG. 3 illustrates some examples of the cleavage portion 102.

For example, a CRISPR-Cas9 system can be used. In this case, the cleavage reagent is a Cas9 protein and a guide RNA, and the cleavage portion 102 includes a target sequence 105A of the guide RNA and a protospacer adjacent motif (PAM) sequence 105B. At this time, the cleavage portion 102 is a double-stranded nucleic acid, and also includes a complementary sequence 105Ac of the target sequence 105A and a complementary sequence 105Bc of the PAM sequence 105B. The target sequence 105A is a sequence of about 20 bases, and includes a PAM sequence 105B on a 3' side. The PAM sequence 105B varies depending on the type of Cas9 protein, but has, for example, a sequence of NGG at a 5' terminal. Here, N is any one of A, T, C, and G. The guide RNA may include a locked nucleic acid (LNA).

Alternatively, it is also possible to use an endonuclease such as a restriction enzyme as a cleavage reagent. In that case, as the cleavage portion 102, a target sequence 105C of the double-stranded nucleic acid of the endonuclease or a target sequence 105D of the single-stranded nucleic acid can be used. As the target sequence 105C, an appropriate target sequence may be used depending on the shell of the endonuclease, and when a restriction enzyme is used, the target sequence may be, for example, a palindromic sequence. As the restriction enzyme, for example, a zinc finger nuclease (ZFN), a transcription activation-like effector nuclease (TALEN), or the like can be used.

Alternatively, His-Tag (registered trademark) can be used. In this case, the cleavage portion 102 includes, for example, His-Tag 15F in which about 6 consecutive histidine residues and Ni-NTA (nickel nitrilotriacetic acid) are bonded to each other, and imidazole or the like can be used as a cleavage reagent.

Alternatively, the cleavage portion 102 may be a substance containing —S—S— bond (disulfide bond) 15G formed by dehydrogenation of a thiol group and a thiol group. In that case, as the cleavage reagent, a reducing agent such as tris (2-carboxyethyl) phosphine (TCEP), dithiothreitol (DTT), or 2-mercaptoethanol (2ME) can be used.

The body to be cleaved 105 is not limited thereto, and various substances cleaved by a specific operation can be used. As illustrated in part (b) of FIG. 2, the same type of the cleavage portion 102 is used between the first to m-th probes.

The reporter portion 103 is preferably a double-stranded nucleic acid as illustrated in part (a) of FIG. 2, but may be a single-stranded nucleic acid. The reporter portion 103 includes a common amplification sequence and a specific amplification sequence.

The common amplification sequence includes at least a first common primer binding sequence 106F and a complementary sequence 106Fc thereof and a second common primer binding sequence 106R and a complementary sequence 106Rc thereof. As illustrated in part (b) of FIG. 2, the same sequence is used as the common amplification sequence between the first to m-th probes, and the same primer set (common primer set) can be combined and amplified.

The specific amplification sequence is disposed in the region amplified by the common amplification sequence, that is, between the first common primer binding sequence 106F and the second common primer binding sequence 106R. The specific amplification sequence includes at least a first specific primer binding sequence 107F and a complementary sequence 107Fc thereof and a second specific primer binding sequence 107R and a complementary sequence 107Rc thereof. The specific amplification sequences are different from each other between the first to m-th probes, and different primer sets (first to m-th specific primer sets) can be bonded and amplified.

Figure 4:
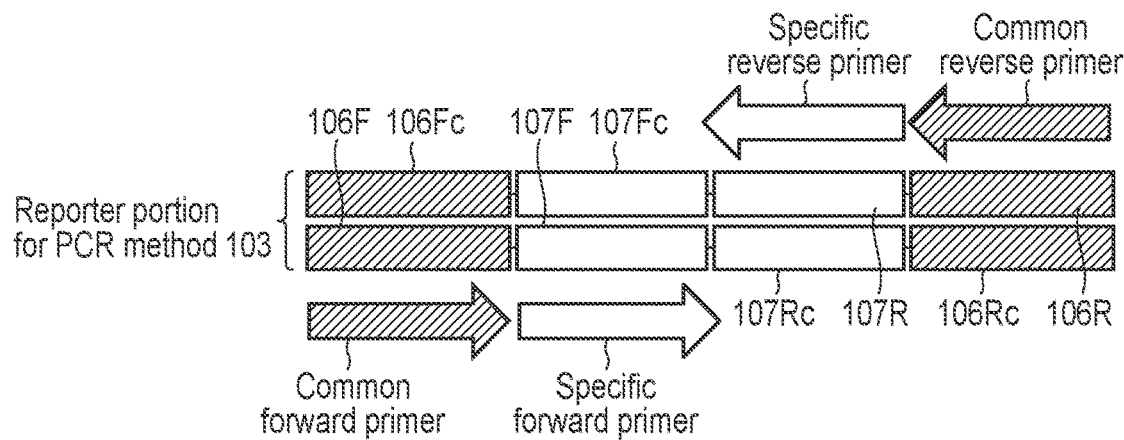
FIG. 4 is a diagram illustrating an example of a reporter portion of the embodiment.

An example of the reporter portion 103 will be described with reference to FIGS. 4 and 5. FIG. 4 illustrates the reporter portion 103 and the corresponding primer set in the case of using the PCR method. For example, the first common primer binding sequence 106F has a sequence with which forward primers of the common primer set for PCR hybridize. The second common primer binding sequence 106R has a sequence with which reverse primers of the common primer set for PCR hybridize. The first specific primer binding sequence 107F has a sequence with which the forward primers of the specific primer set for PCR hybridize. The second specific primer binding sequence 107R has a sequence with which reverse primers of the specific primer set for PCR hybridize.

The same common primer set for PCR is used between the first to m-th probes 100, and different specific primer sets for PCR are used between the first to m-th probes 100.

Figure 5:
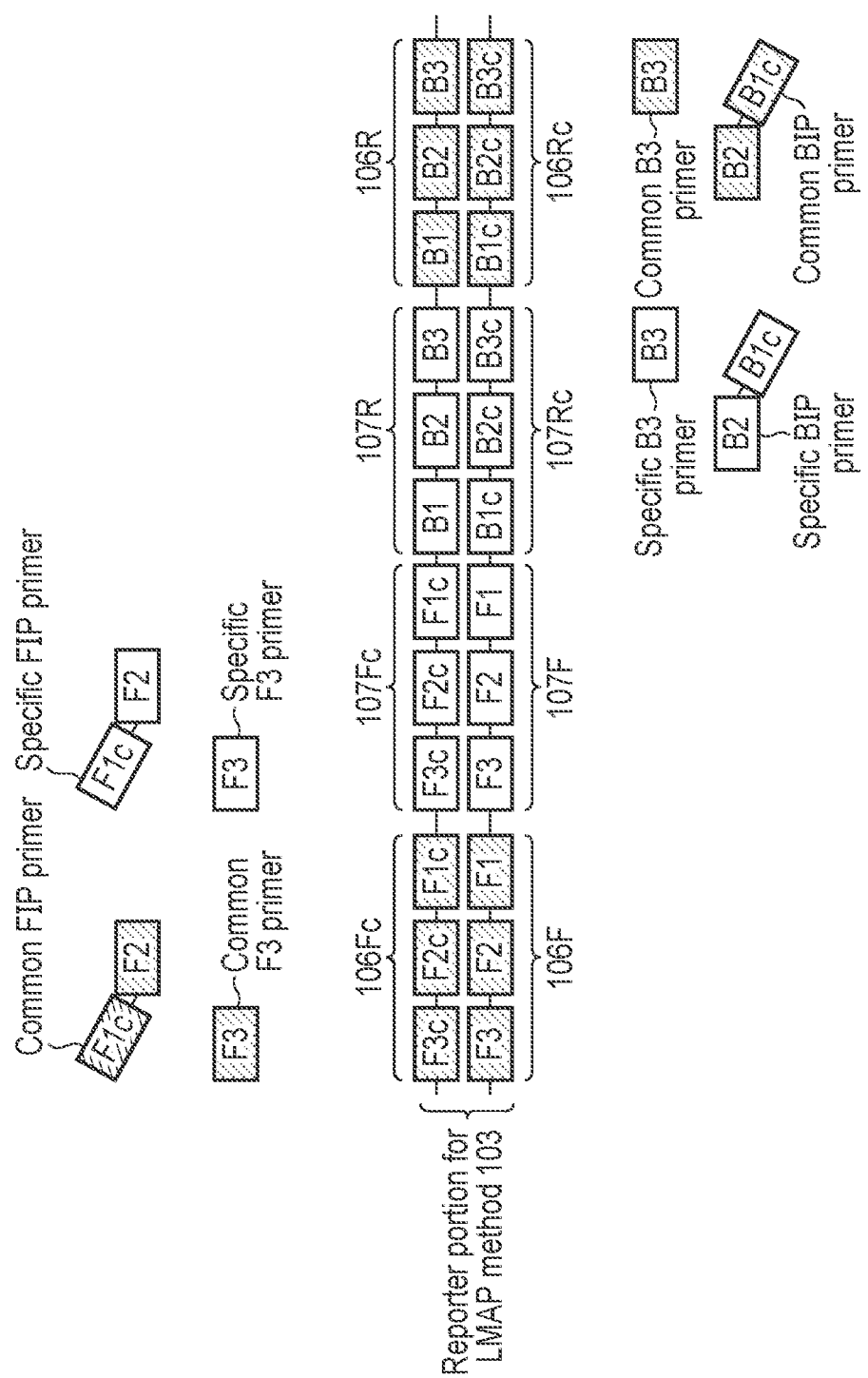
FIG. 5 is a diagram illustrating an example of the reporter portion of the embodiment.

FIG. 5 illustrates the reporter portion 103 and the corresponding primer set in the case of using the LAMP method. In this case, the first common primer binding sequence 106F includes a region in which an FIP primer and an F3 primer of the common primer set for LAMP are bonded to each other, that is, an F3 region, an F2 region, and an F1 region. The second common primer binding sequence 106R includes a region in which an BIP primer and a B3 primer of the common primer set for LAMP are bonded to each other, that is, a B3 region, a B2 region, and a B1 region. The first specific primer binding sequence 107F includes a region in which the FIP primer and the F3 primer of the specific primer set for LAMP are bonded to each other, that is, an F3 region, an F2 region, and an F1 region. The second specific primer binding sequence 107R includes a region in which an BIP primer and a B3 primer of the specific primer set for LAMP are bonded to each other, that is, a B3 region, a B2 region, and a B1 region.

The same common primer set for LAMP is used between the first to m-th probes 100, and different specific primer sets for LAMP are used between the first to m-th probes 100.

The amplification method is not limited to the PCR method and the LAMP method, and other amplification methods such as a real-time PCR method and a NASBA method may be used, and a primer binding sequence corresponding to a desired amplification method may be provided to the common amplification sequence and the specific amplification sequence. The common amplification sequence and the specific amplification sequence may include sequences corresponding to the same amplification method, or may include sequences corresponding to different amplification methods.

In the case of using the real-time PCR method, a TaqMan (registered trademark) probe binding sequence may be inserted into the reporter portion 103 of the probe 100. In that case, it is preferable to insert a TaqMan probe binding sequence between the first specific primer binding sequence 107F and the second specific primer binding sequence 107R. With this, the presence or absence of the specific sequence can be detected in real time. Alternatively, the TaqMan probe binding sequence may be inserted between the first common primer binding sequence 106F and the second common primer binding sequence 106R. In this case, whether or not the reporter portion 103 is present can be detected in real time.

When base lengths of sequences between the first common primer binding sequence 106F and the second common primer binding sequence 106R are different from those between the first to m-th probes 100, or when these sequences include a sequence that easily forms a guanine 4 heavy chain structure, the amplification efficiency is different between the first to m-th probes 100, and there is a possibility that a bias occurs in the amount of amplification products. Therefore, it is preferable that the sequence between the first common primer binding sequence 106F and the second common primer binding sequence 106R has the same base length and guanine base ratio, and does not contain a sequence that easily forms a guanine 4 heavy chain, for example, (TTAGGG)n or (TTGGGG)n.

In addition, as in a probe 110 illustrated in FIG. 6, spacers 1S to 5S may be provided between the respective portions and the respective sequences. The spacer is made of a substance or nucleic acid that does not adversely affect the function of each portion and each sequence.

For example, the nucleic acid region of the reporter portion 103 and, if necessary, the binding portion 101 is preferably a double-stranded nucleic acid. By using the double-stranded nucleic acid, an unnecessary aptamer action unique to a single strand is suppressed, and the degradation resistance by an exonuclease that can be contained in a specimen is improved. Further, the region of the nucleic acid can be formed of, for example, DNA or RNA, and may contain an artificial base. For example, a double strand of LNA and DNA or LNA and RNA may be used. In that case, exonuclease resistance is further improved, and endonuclease resistance is also improved.

However, there is also a region where it is not preferable to use the LNA. For example, when a restriction enzyme is used, it is preferable that a palindromic sequence part of the target sequence 105C does not contain LNA. In addition, when the CRISPR-Cas9 system is used, it is preferable that the PAM sequence 105B does not contain LNA. Furthermore, when LNA is used as the target sequence of the guide RNA, it is preferable that LNA is used as the sequence 15A to which the guide RNA binds and the complementary sequence 15Ac does not contain LNA. When the reporter portion 103 is a double-stranded nucleic acid, it is preferable that at least one strand does not contain LNA.

For example, in the example of the probe 110 of FIG. 6, it is conceivable that (1) 1S, 105A, 2S, 106F, 3S, 107F, 4S, 107Rc, 5S, and 106Rc contain LNA, or (2) 1cS, 105Ac, 2c5, 106Fc, 3c5, 107Fc, 4c5, 107R, 5c5, and 106R contain LNA.

In a further embodiment, a probe 120 illustrated in part (a) of FIG. 7 may not include the cleavage portion 102. In that case, the reporter portion 103 is a double-stranded nucleic acid, and the reporter portion 103 is denatured by heating or adjusting the salt concentration, and as illustrated in part (b) of FIG. 7, the strand not linked to the binding portion 101 of the reporter portion 103 is liberated, thereby separating the reporter portion 103. In this case, if the liberated strand contains an artificial base such as LNA, amplification may be inhibited, and thus it is preferable to design the liberated strand so as not to contain an artificial base.

Hereinafter, the procedure of the analysis method of the embodiment will be described. As illustrated in FIG. 1, the analysis method includes the following steps: dispensing a specimen into $first_1$ to $first_n$ containers configured to capture a target particle (first dispensing step S1); removing a contaminant other than the target particle to be captured from the specimen (contaminant removing step S2); adding first to m-th probes to the $first_1$ to $first_n$ containers, the first to m-th probes having at least a binding portion that specifically binds to any one of first to m-th surface markers of the target particle and a nucleic acid reporter portion including a common amplification sequence to which a common primer set binds and a specific amplification sequence to which a specific primer set binds and which is disposed in a region amplified by the common amplification sequence, in which the binding portion and the specific amplification sequence are different from each other between the first to m-th probes (probe adding step S3); removing excessive first to m-th probes that have not bound to the target particle (probe removing step S4); individually amplifying the reporter portion for each of the $first_1$ to $first_n$ containers using the common primer set to obtain first to n-th amplification products (first amplifying step S5); removing an excessive common primer set from the first to n-th amplification products (primer set removing step S6); dispensing the first to n-th amplification products into $second_1$ to $second_m$ containers respectively (second dispensing step S7); further amplifying the amplification products in the $second_1$ to $second_m$ containers using the first to m-th specific primer sets, respectively (second amplifying step S8); and analyzing presence or absence or types of the target particles captured in the $first_1$ to $first_n$ containers by determining the types of surface markers present in the $first_1$ to $first_n$ containers from the presence or absence of the amplification product by the specific primer set in the $second_1$ to $second_m$ containers (analyzing step S9).

Here, n and m are integers of 2 or more.

Each of the above steps will be described below.

(First Dispensing Step S1)

Figure 8:
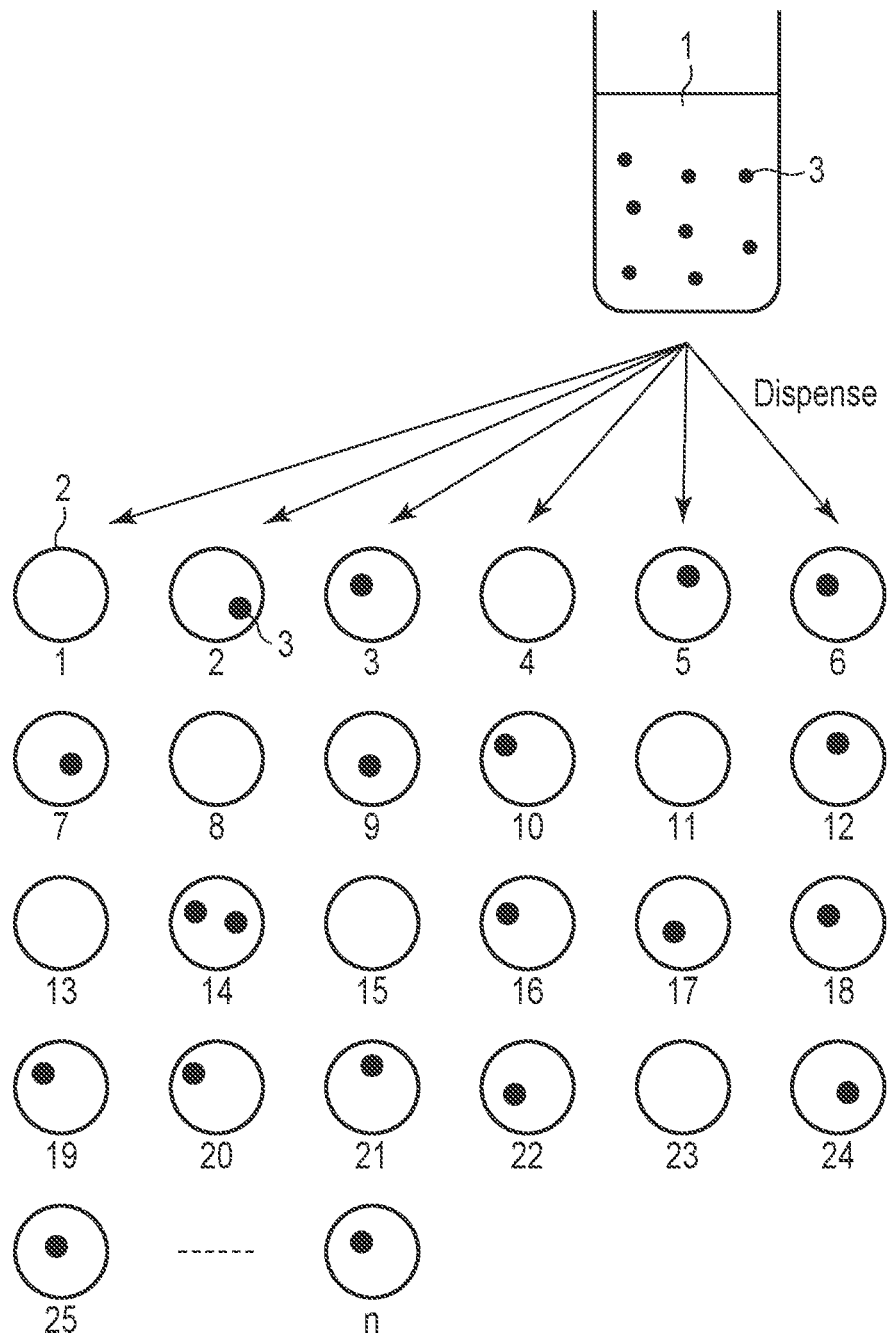
FIG. 8 is a diagram illustrating an example of a dispensing procedure of the analysis method of the embodiment.

A first dispensing step S1 will be described with reference to FIG. 8. In this step, a specimen 1 is dispensed into n first containers 2 ($first_1$ to $first_n$ containers) in equal amounts. Hereinafter, the n first containers 2 are also collectively referred to as first containers 2. The number n of the first containers 2 may be, for example, 2 to 50,000, and is more preferably 50 to 20,000. It is preferable that the $first_1$ to $first_n$ containers 2 are arranged in a matrix form because it is easy to manufacture and handle. Alternatively, the containers may be arranged linearly, randomly, or the like.

Each of the first containers 2 includes a capturing mechanism for capturing target particles 3. For example, the region for capturing the target particles 3 in each first container 2 is preferably about 150 nm×150 nm, for example.

After dispensing, it is preferable that 0 to several target particles 3 are captured in each first container 2. The number is more preferably 0 or 1. In a case where the concentration of the target particles 3 of the specimen 1 is so high as to exceed the number of captured particles, it is preferable to dilute the specimen 1 before dispensing in order to obtain the preferable number of captured particles as described above. The dilution can be performed by, for example, a limiting dilution method or the like. For example, the limiting dilution refers to diluting the specimen to a concentration lower than the concentration at which two target particles are contained in the $first_1$ to $first_n$ containers, and the dispensing can be performed after the limiting dilution. For example, dispensing is performed after dilution to a final concentration at which the concentration of the target particles 3 in the specimen 1 satisfies the following condition: the final concentration (number of target particles/volume of specimen) <(2/internal volume of one of the $first_1$ to $first_n$ containers). For example, the dilution can be performed by adding an appropriate solvent corresponding to the type of the specimen 1 to the specimen 1 in a desired amount. The suitable solvent is preferably, for example, water, a buffer solution, physiological saline, or the like. Before dispensing, the specimen 1 may be pretreated by ultracentrifugation or the like as necessary.

Alternatively, the first container 2 having a sensor function may be used to detect the number of the target particles 3 captured after dispensing, estimate the concentration of the target particles 3 in the specimen 1, and dilute the specimen 1 so as to obtain a preferable number of captured target particles 3. The first container 2 having a sensor function will be described later in detail.

The capturing mechanism may be, for example, a capturing body fixed to any inner surface such as a bottom surface of the first container 2. The capturing body is, for example, a substance that binds to the target particle 3 such as an antibody, an aptamer, a nucleic acid, a protein, or a peptide, and can be selected according to the type of the target particle 3. For example, a phosphasylserine-binding molecule (Annexin, Tim4 protein (T-cell immunoglobulin domain and mucin domain-containing protein 4), and the like) that binds to the lipid bilayer membrane of the exosome, an antibody (Anti-CD9 antibody, anti-CD63 antibody, anti-CD81 antibody, and the like) that binds to an exosome surface marker protein, a sugar chain (Neu5Acalpha 2,3Gal type, Neu5Acalpha 2,6Gal type, and the like) that binds to hemagglutinin of influenza virus, ACE2 (angiotensin converting enzyme II) that binds to a spike protein of coronavirus, and the like can be used as the capturing body; however, the capturing body is not limited thereto.

Alternatively, the capturing mechanism may be a dielectrophoresis device. For example, two electrodes are provided so as to sandwich the space inside first container 2 between the bottom surface and the top surface. When the area of the electrode on the top surface is made larger than that of the electrode on the bottom surface in plan view, and a voltage is applied between both electrodes, it is possible to guide the target particles 3 to the bottom by dielectrophoresis. Alternatively, the target particle 3 may be guided to the bottom using electrophoresis. Alternatively, the target particle 3 may be captured using magnetism, and an example thereof will be described later.

Each of the first containers 2 does not necessarily need to be isolated at this time, and each of the capturing mechanisms may be independently arranged at intervals.

(Contaminant Removing Step S2)

Figure 9:
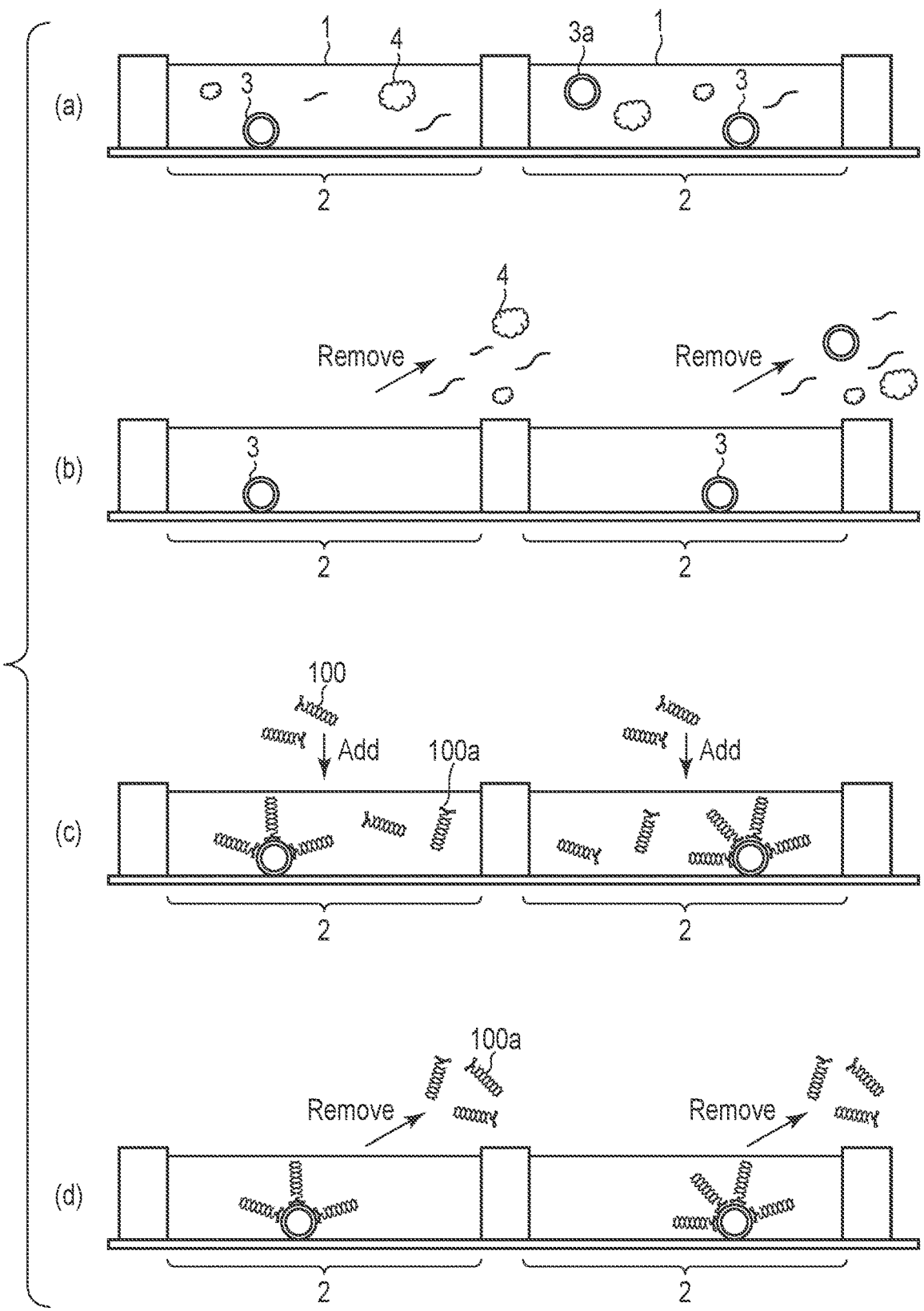
FIG. 9 is a diagram illustrating an example of procedures of contaminant removal, probe addition, and probe removal in the analysis method of the embodiment.

Part (a) of FIG. 9 illustrates the first container 2 into which the specimen 1 is dispensed. FIG. 9 illustrates two adjacent first containers 2 among the n first containers 2 for convenience. After dispensing, each first container 2 contains the captured target particles 3 (hereinafter, also referred to as "target particle to be captured 3") and other contaminants 4. The contaminant 4 includes an excessive target particle 3a, a protein, a peptide, a nucleic acid, a high-molecular compound, and/or a low-molecular compound that have not been captured.

In the contaminant removing step S2, the contaminants 4 are removed as illustrated in part (b) of FIG. 9. For example, the contaminants 4 can be removed by discharging the specimen 1 and adding a new solvent in a state where the target particle 3 is captured. As a removing method, an appropriate means may be used according to the shape of the first container 2, and a specific example will be described later.

(Probe Adding Step S3)

Next, as illustrated in part (c) of FIG. 9, first to m-th probes 100 are added to each first container 2. When the target surface marker is present in the captured target particle 3, the probe 100 having the binding portion 101 corresponding thereto binds thereto. When one target particle 3 has a plurality of types of target surface markers, the plurality of types of probes 100 bind to each other.

(Probe Removing Step S4)

In each first container 2, there may be excessive probes 100a which have not bound to the target particles 3. In the probe removing step S4, the excessive probes 100a are removed as illustrated in part (d) of FIG. 9. As a removing method, an appropriate means may be used according to the type of the first container 2, and a specific example will be described later.

(First Amplifying Step S5)

Next, the reporter portion 103 is amplified. Before the amplification, the reporter portion 103 may be separated from the probe 100. At this time, at least before separation, the liquid contained in each of the first containers 2 is isolated using a partition wall or the like. A specific example thereof will be described later.

For example, the separation is performed by adding the cleavage reagent 6 as illustrated in part (e) of FIG. 10. Alternatively, in a case of using the probe 120 not including the cleavage portion 102, the double-stranded nucleic acid of the reporter portion 103 is separated into a strand linked to the binding portion 101 and a strand not linked to the binding portion 101 by heating or decreasing the salt concentration. As a result, a strand not linked to the binding portion 101 is released. When the probe 100 including the binding portion 101 is used, separation may be performed by this method. However, when heating or reducing the salt concentration, the captured target particles 3 may be damaged. Therefore, by performing cleavage using a cleavage reagent, heating becomes unnecessary, and it is not necessary to set the salt concentration to a low concentration with poor biocompatibility, so that it can be used for subsequent analysis (Genome, proteome, metabolome) in a state where the target particle 3 is suppressed from being damaged.

In this way, the reporter portion 103 can be separated as illustrated in part (f) of FIG. 10. As a result, the reporter portion group 7 is obtained for each of the first containers 2. The reporter portion group 7 includes the reporter portion 103 of the probe 100 corresponding to the target surface marker according to the type of the target particle 3 captured in the first container 2.

For example, in the example of Table 1 above, the reporter portion group 7 including the reporter portions 103 of the first, second, and third probes respectively bound to the target surface markers a, b, and c is obtained from the first container 2 in which the target particle A is captured, the reporter portion group 7 including the reporter portions 103 of the first, third, and fourth probes respectively bound to the target surface markers a, c, and d is obtained from the first container 2 in which the target particle B is captured, the reporter portion group 7 including the reporter portions 103 of the second, fifth, and sixth probes respectively bound to the target surface markers b, e, and f is obtained from the first container 2 in which the target particle C is captured, the reporter portion group 7 including the reporter portions 103 of the third and fifth probes respectively bound to the target surface markers c and e is obtained from the first container 2 in which the target particle D is captured, and the reporter portion 103 is not obtained from the first container 2 in which the target particle 3 is not captured or the first container 2 in which the target particle 3 not including the target surface marker is captured.

Hereinafter, each of the reporter portion groups 7 obtained in the first$_1$ to first$_n$ containers 2 is referred to as a first to n-th reporter portion group 7, respectively.

After that, the reporter portion 103 included in the reporter portion group 7 is amplified, but before the amplification, the reporter portion group 7 may be collected in another container as illustrated in part (g) of FIG. 10. In the case of collection, each reporter portion group 7 is individually collected from the first$_1$ to first$_n$ containers 2, and amplification is individually performed in each of the reporter portion groups 7 without mixing them.

The amplification may be performed in the first container 2 without collecting the reporter portion group 7, but in this case, the captured target particle 3 may be damaged, and thus it is preferable to perform the amplification after collecting the target particle 3 in another container when the target particle 3 is used later.

In the first amplifying step S5, as illustrated in parts (h) and (i) of FIG. 10, a common primer set and an amplification reagent are added to all of the first to n-th reporter portion groups 7, and maintained under the amplification conditions. A sufficient amount of the common primer set can be added to each reporter portion group 7. The amplification reagent may be an appropriate known reagent according to the amplification method to be used. For example, the amplification reagent contains at least DNA polymerase and deoxynucleoside triphosphate (dNTP: dATP, dTTP, dGTP, dCTP) as a substrate, and further contains a salt, a buffer for pH adjustment, a surfactant, and the like as necessary. When the real-time PCR method is used, in the case of the intercalator method, the amplification reagent contains an intercalator such as TB Green. Alternatively, in the case of a 5'-nuclease method, such as TaqMan from Thermo Fisher, the amplification reagent contains a quencher and an oligonucleotide chimerically labeled with fluorescence.

The amplification condition may be an appropriate temperature condition selected according to the amplification method to be used. For example, when the PCR method is used, the temperature cycle is maintained at a temperature suitable for thermal denaturation, annealing, and extension, and when the LAMP method is used, the temperature cycle is maintained at an appropriate isothermal condition. In the first amplifying step S5, the sequence between the first common primer binding sequence 106F and the second common primer binding sequence 106R is amplified by using the common primer set described above. As a result, each reporter portion 103 included in the reporter portion group 7 is uniformly amplified. As a result, first to n-th amplification products 8 corresponding to first$_1$ to first$_n$ containers 2, respectively, are obtained.

Although the example of separating the reporter portion 103 has been described above, the first amplifying step S5 may be performed without separating the reporter portion 103. As a method for amplifying the reporter portion 103 without separating the reporter portion 103, amplification is performed in the first container 2 without separating the reporter portion 103. In that case, since the target particle 3 to be captured may be damaged, when the target particle 3 is used later, it is preferable that the reporter portion 103 is separated, collected, and amplified. In addition, when the amplification is performed in the first container 2, contaminants from the target particle 3 may become noise that inhibits the amplification. In addition, when RNA or DNA present in or around the target particle 3 has the same sequence as or a sequence close to the sequence of the common primer, there is a possibility of erroneous replication. Therefore, by separating the reporter portion 103, the risk that contaminants from the target particle 3 inhibit the amplification and the risk that RNA and DNA present in or around the target particle 3 are erroneously replicated can be reduced, and more specific amplification and highly accurate analysis can be performed.

(Primer Set Removing Step S6)

Thereafter, as illustrated in part (j) of FIG. 10, the excessive common primer set is removed from the amplification product 8 to obtain the amplification product 8a after purification. As a method for removing the primer set, for example, when the amplification product 8 is collected using a nucleic acid adsorption purification column such as Diffinity RapidTip (registered trademark) manufactured by Merc Corporation, an unnecessary primer set is removed.

By removing the excessive common primer set, the amplification by the common primer set can be suppressed. In the second amplifying step S8 to be described later, an increase in the amplification product is detected, but there is a possibility that amplification occurs even if the amplification product is amplified with the common primer in the second amplifying step S8. Therefore, by removing the excessive common primer set, such undesired detection can be further reduced. The primer set removing step S6 is not limited to completely removing the common primer set, and the common primer set may remain without being removed as long as the detection sensitivity is not degraded.

(Second Dispensing Step S7)

Figure 11:
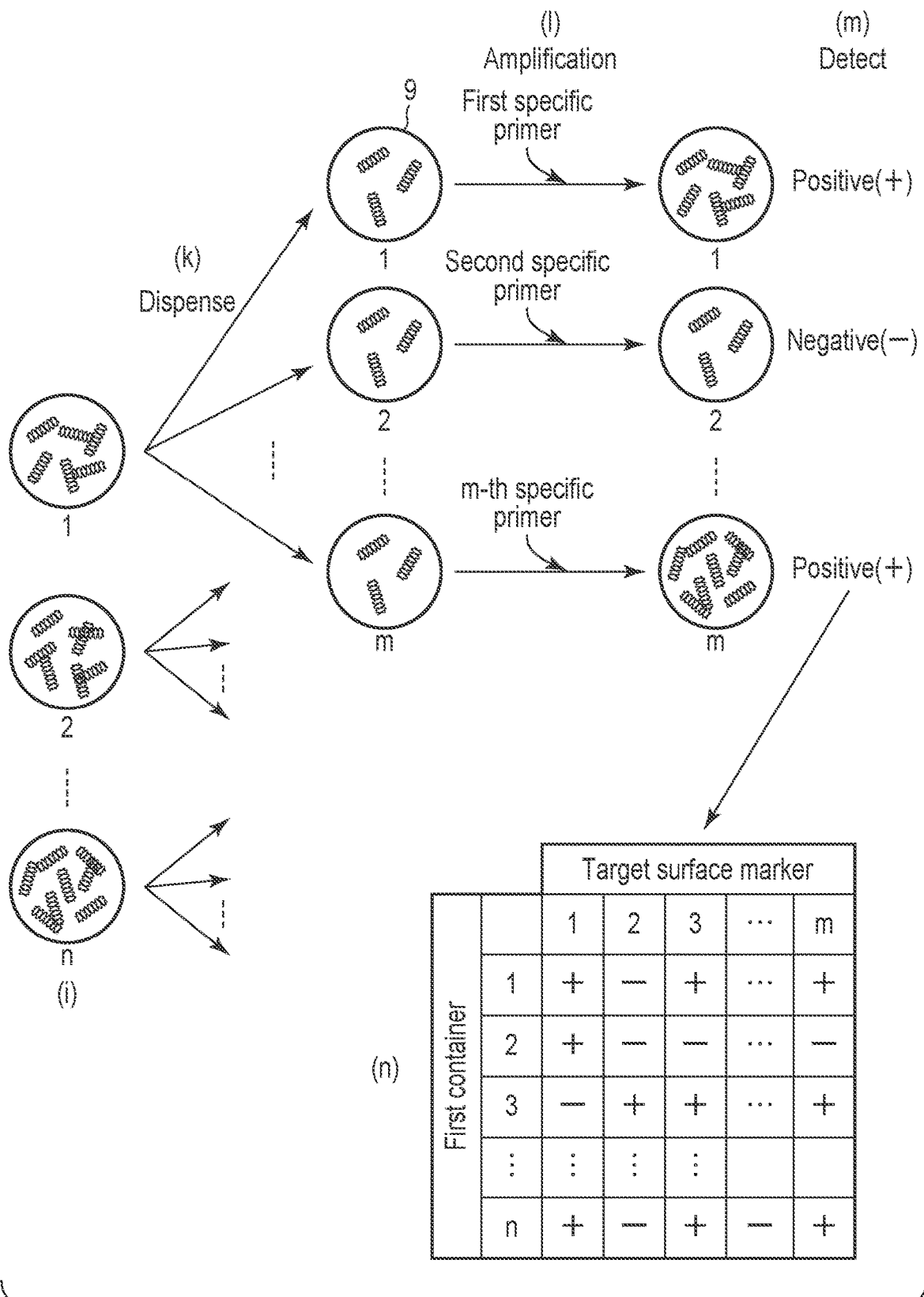
FIG. 11 is a diagram illustrating an example of procedures of dispensing, further amplifying, and detecting an amplification product in the analysis method of the embodiment.

Next, as illustrated in part (k) of FIG. 11, the first to n-th amplification products 8a are respectively dispensed into m second containers 9 (second$_1$ to second$_m$ containers 9), that is, the same number as the number of types of the probes 100 used. m (second$_1$ to second$_m$)×n sets (first to n-th amplification products) of the second containers 9 are prepared. The first amplification product 8 is dispensed in equal amounts to the first set of second$_1$ to second$_m$ containers 9, and the second amplification product 8 is dispensed in equal amounts to the second set of second$_1$ to second$_m$ containers 9, and this is performed up to the n-th amplification product 8.

When real-time PCR or the like is used in the first amplifying step S5, a container in which the reporter portion group 7 is absent (that is, an amplification product of the reporter portion 103 is not generated) can be known from the fact that no amplified signal is observed. In a case where the reporter portion group 7 is absent, useful information cannot be obtained even if the subsequent second amplifying step S8 is performed. Therefore, for a container in which no amplified signal is observed in the first amplifying step S5, the steps after the second dispensing step S7 can be omitted.

(Second Amplifying Step S8)

Next, as illustrated in part (l) of FIG. 11, a specific primer set and an amplification reagent are added to each dispensed amplification product and maintained under the amplification conditions. Here, the specific primer set and the amplification reagent have been described above. m types of specific primer sets are prepared corresponding to the first to m-th probes 100 (these specific primer sets are referred to as "first to m-th specific primers"). The first to m-th specific primer sets are added to the second$_1$ to second$_m$ containers 9, respectively. That is, the first specific primer set is added to the second$_1$ container 9, the second specific primer set is added to the second$_2$ container 9, and this is repeated until the m-th specific primer set. Such a specific primer set is added for the first to n-th sets. Thereafter, all the second containers 9 are maintained under the amplification conditions. The amplification condition may be an appropriate condition according to the amplification method to be used.

At this time, it is preferable to add the complementary base sequence of the common primer set together with the specific primer set in order to deactivate (knock down) the residual portion that has not been removed by the nucleic acid adsorption column or the like among the common primer set used previously. In order to confirm whether the deactivation by the removal of the common primer set or the addition of the complementary sequence in the primer set removing step S6 is sufficient, it is also possible to further add a TaqMan probe for common amplification. When the fluorescent color of the TaqMan probe is changed between that for the common amplification and that for the specific amplification, it can be confirmed whether there is undesired amplification by the common primer set in the second amplifying step S8. In the case of confirming the residual of the common primer set using the Taqman probe, the TaqMan probe binding sequence for common amplification is arranged outside the first specific primer binding sequence 107F and the second specific primer binding sequence 107R.

(Analyzing Step S9)

After the second amplifying step S8, an amplification product is detected in each second container 9 as illustrated in part (m) of FIG. 11. When the amplification product is produced in a certain second container 9 (Positive (+)), it means that the reporter portion 103 of the corresponding probe 100 that can be amplified by the specific primer set added thereto was present in the second container 9. For example, in particular second$_1$ to second$_m$ containers 9 of a particular set, if it was Positive (+) in several second containers 9, it can be seen that the target surface marker corresponding to the number of the second container 9 is present in the first container 2 corresponding to the number of the set. By obtaining this information in each set, for example, as illustrated in part (n) of FIG. 11, the presence or absence of the first to m-th target surface markers in the first$_1$ to first$_n$ containers (corresponding to the above 1 to n sets) can be represented in a table. In addition, it is possible to determine the type of the target particle 3 contained in the first container 2 corresponding to the set from the type of the target surface marker present in a certain first container 2. It is possible to obtain information such as the type and number of the plurality of target particles 3 contained in the specimen 1 by performing the processing for the first$_1$ to first$_n$ containers 2.

In this manner, the target particle 3 in the specimen 1 can be analyzed.

According to the analysis method of the present embodiment, it is possible to simultaneously and comprehensively analyze a plurality of target particles 3 in the specimen 1, for example, tens of thousands of target particles 3. For example, it is possible to know what type and how many target particles 3 are present in the specimen 1 (composition of the target particles 3). For example, it is also possible to analyze information of a cell in which the target particle 3 is produced, information of a cell to which the target particle 3 is transferred, or the like from the type of the target particle 3 and/or the type of the surface marker thereof. As a result, for example, a large number of pieces of information regarding the presence or absence or metastasis of cancer, the presence or absence or transportation of causative substances of diseases other than cancer, the infection status of viruses, and the like can be obtained at a time. This information can be used, for example, for early diagnosis of a disease, prognostication, and the like.

In one embodiment, step from S1 to S9 may be continuously carried out without performing another step between any of these steps.

(Method Using Magnetic Beads)

In a further embodiment, a method using magnetic beads is provided. In the present method, as illustrated in parts (a) and (b) of FIG. 12, first, magnetic beads 10 capable of binding to the target particles 3 are added to the specimen 1. The magnetic beads 10 are surface-processed so as to bind to the target particle 3, for example. The magnetic beads 10 are added at a sufficiently high concentration relative to the expected amount of the target particles 3. For example, the amount of the magnetic beads 10 added to the specimen may be an amount in which the concentration of the magnetic beads 10 is higher than the concentration of the target particles in the specimen. As a result, a state is brought about where one, or rarely, a plurality of target particles 3 are bonded to one magnetic bead 10, or no target particles 3 are bonded thereto.

Figure 12:
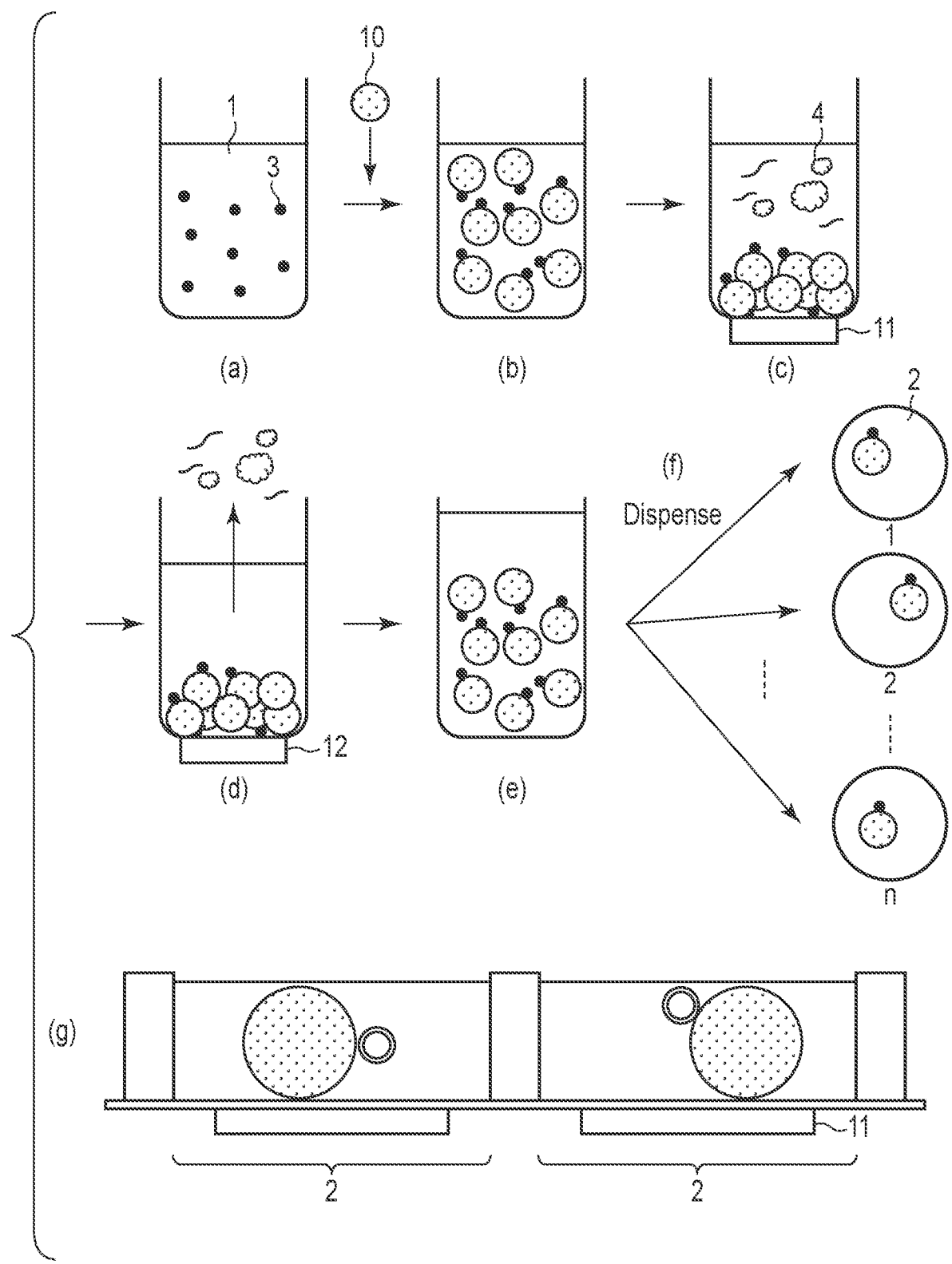
FIG. 12 is a diagram illustrating an example of a procedure using magnetic beads of the embodiment.

Next, as illustrated in part (c) of FIG. 12, by substituting the solution (solvent) in a state where the magnetic beads 10 are fixed to, for example, the bottom of the container using magnetism (for example, by a magnetism generator 11 such as a magnet), contaminants 4 are washed and removed as illustrated in part (d) of FIG. 12. Therefore, in the present method, since the contaminants 4 can be collected at a time from the container containing the specimen 1 before the first dispensing step S1, the procedure is more simple and preferable.

Next, as illustrated in part (e) of FIG. 12, the magnetism is released to redisperse the magnetic beads, and then, as illustrated in part (f) of FIG. 12, the specimen containing the magnetic beads 10 is dispensed into the first$_1$ to first$_n$ containers 2 (first dispensing step S1). At this time, for example, dispensing is performed after diluting the specimen so that the concentration of the magnetic beads 10 in the specimen containing the magnetic beads 10 is lower than the concentration at which the two magnetic beads are accommodated in the first$_1$ to first$_n$ containers.

In this case, as illustrated in part (g) of FIG. 12, the first container 2 includes, for example, a magnetism generator 11 as a capturing mechanism on the bottom surface. Subsequent steps S3 to S9 can be performed in the same manner as in the method not using magnetism, but the probe removing step (S4), and collection of the reporter portion 103 as necessary can be performed by generating magnetism by the magnetism generator 11 and collecting the magnetic beads 10 on the bottom surface.

Note that a step of washing and removing the contaminants 4 illustrated in parts (c) and (d) of FIG. 12 may be performed after dispensing into the first$_1$ to first$_n$ containers 2. In this case, after the magnetic beads 10 are added to the specimen 1, the mixture is diluted to a concentration at which one magnetic bead 10 is contained or not contained in each of the first$_1$ to first$_n$ containers 2 while containing the contaminant 4, and the mixture is dispensed. That is, the magnetic beads 10 are diluted to a concentration lower than the concentration at which two magnetic beads are contained in the first$_1$ to first$_n$ containers and the mixture is dispensed. For example, dispensing is performed after dilution to a final concentration at which the concentration of the magnetic beads 10 in the specimen 1 satisfies the following condition: the final concentration (number of magnetic beads/volume of specimen)<(2/internal volume of one of the first$_1$ to first$_n$ containers). Thereafter, the magnetic beads 10 are fixed to, for example, the bottom of the container or the like by the magnetism generator 11 provided in the first$_1$ to first$_n$ containers 2, and the contaminants 4 are washed and removed.

(Method Using First Container Having Sensor Function)

Figure 13:
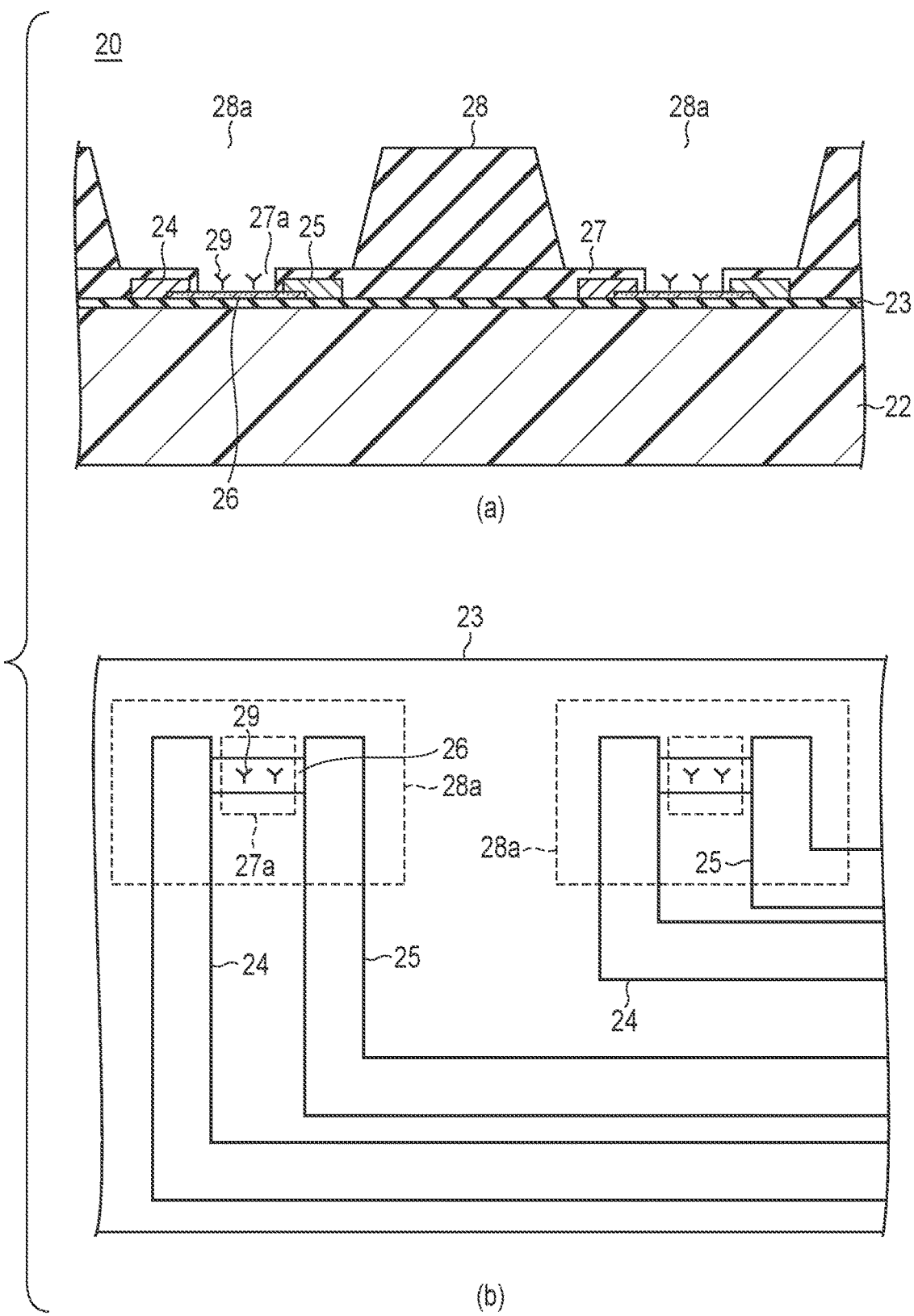
FIG. 13 is a diagram illustrating an example of a first container of the embodiment.

An example of the first container 20 having a sensor function will be described with reference to FIG. 13. Part (a) of FIG. 13 is a cross-sectional view of the first container 20, and part (b) of FIG. 13 is a plan view. FIG. 13 illustrates two adjacent containers among the n first containers 20 for convenience.

The plurality of first containers 20 may be formed, for example, on one substrate 22. An insulating film 23 is further stacked on the substrate 22.

The first container 20 includes at least: a first electrode 24 and a second electrode 25 disposed on the insulating film 23 at an interval; a channel 26 having one end electrically connected to the first electrode 24 and the other end connected to the second electrode 25, through which a current flowing between the first electrode 24 and the second electrode 25 passes, and an insulator 27 stacked on the first electrode 24 and the second electrode 25 and covering the two electrodes. The insulator 27 is provided with an opening 27a so that the surface of the channel 26 opposite to the substrate 22 is exposed.

In addition, a partition wall 28 may be formed to isolate the liquid contained in each of the first containers 20 from the adjacent first containers 20. The partition wall 28 is formed of, for example, an insulating material, and can be formed by stacking this material on the insulator 27 and providing a partition wall opening 28a on the channel 26 of each first container 20.

In addition, for example, a capturing body 29 that captures the target particle 3 is fixed on the exposed surface of the channel 26. Alternatively, another capturing mechanism may be provided, and in the case of a method using the magnetic beads 10, for example, a plurality of mechanism generators arranged in accordance with the position of the channel 26 of each first container 2 may be provided in the substrate 22. When dielectrophoresis is used, for example, an additional electrode having a large area facing the channel 26 is provided above the opening 27*a*.

Although not illustrated, each of the first electrode 24 and the second electrode 25 can be connected to a circuit including a voltage application circuit that applies a voltage between both electrodes and a current measurement circuit that measures a current value flowing between both electrodes.

When the specimen 1 is accommodated in such a first container 20, the resistance of the channel 26 fluctuates when the target particle 3 is captured by the capturing body 29 or approaches the channel 26, and the current value between the first electrode 24 and the second electrode 25 changes. The number of target particles 3 contained in the first container 20 can be detected from the amount of change in the current value. For example, when the target particle 3 is a virus, it can be detected that the current value changes due to the negative charge of the virus.

The channel 26 is preferably a graphene nanoribbon with a width of about 100 to 500 nm and a length of about 200 nm, for example. The width is more preferably 100 nm. When such a graphene nanoribbon is used, the resistance of the channel 26 greatly fluctuates only by attaching one target particle 3. A carbon nanotube having a similar channel width may be used.

Further, one side of the opening 27*a* on the channel 26 is preferably about 150 nm, for example. One side of the partition wall opening 28*a* surrounded by the partition wall 28 is preferably about a little less than 1 mm to several mm. Alternatively, one side of the partition wall opening 28*a* is preferably about 5 μm. The former is suitable for supplying and collecting the solution to and from the first container 20 with a pipette, and the latter is suitable for supplying and collecting the solution using a microchannel.

The widths of the first electrode 24 and the second electrode 25 are preferably about 1 to 10 μm.

When the first container having a sensor function is used, the number of target particles 3 captured by each first container 2 in the first dispensing step S1 can be detected. In addition, in the probe adding step S3, the presence or absence of the probe 100 in the first container 2, the presence or absence of the target particle 3 to which the probe 100 is bonded, and the like can be detected by detecting the charge of the probe 100. At that time, by modifying the probe 100 with a label having a charge, the presence or absence of the probe 100 can be more sensitively distinguished from the contaminant 4 and detected. As the label having a charge, for example, a nucleic acid, a negative charge group such as phosphoric acid, aspartic acid, or glutamic acid, a positive charge group such as lysine, arginine, or histidine, or the like can be used.

As the first container 20 having a sensor function, a two-dimensional sensor such as a CMOS image sensor or a silicon photomask may be used. In this case, for example, a plurality of sensor elements is arranged in an array on substantially the entire bottom of the first container 2. In addition, the capturing body 29 is formed at a desired position on sensor element portions arranged in an array. For example, the capturing body 29 is formed in center of the sensor element portion with a size of about 100 nmΩ. A CMOS image sensor may have low sensitivity for directly reading 100 nm particles. In that case, for example, by modifying the probe 100 with a label that emits an optical signal and detecting the modified probe, it is possible to more sensitively distinguish the probe from the contaminants 4 and detect the target particle 3. The label can be detected by time-resolved observation using a long-life fluorescent dye such as a lanthanoid complex. Alternatively, it is also possible to detect using plasmon scattering. In the case of using these two-dimensional sensors, it is also possible to detect the presence of the target particle 3 and the contaminant 4 attached to a place other than a desired place. With this, it is possible to efficiently detect whether or not the target particle and the contaminant have been removed after the contaminant removing step S2.

(Example of Difference in Procedure due to Difference in Shape of First Container)

The shape of the first container 2 is not limited to that described above. Hereinafter, an example of the procedure of the analysis method in the first containers 2 having different shapes will be described.

Figure 14:
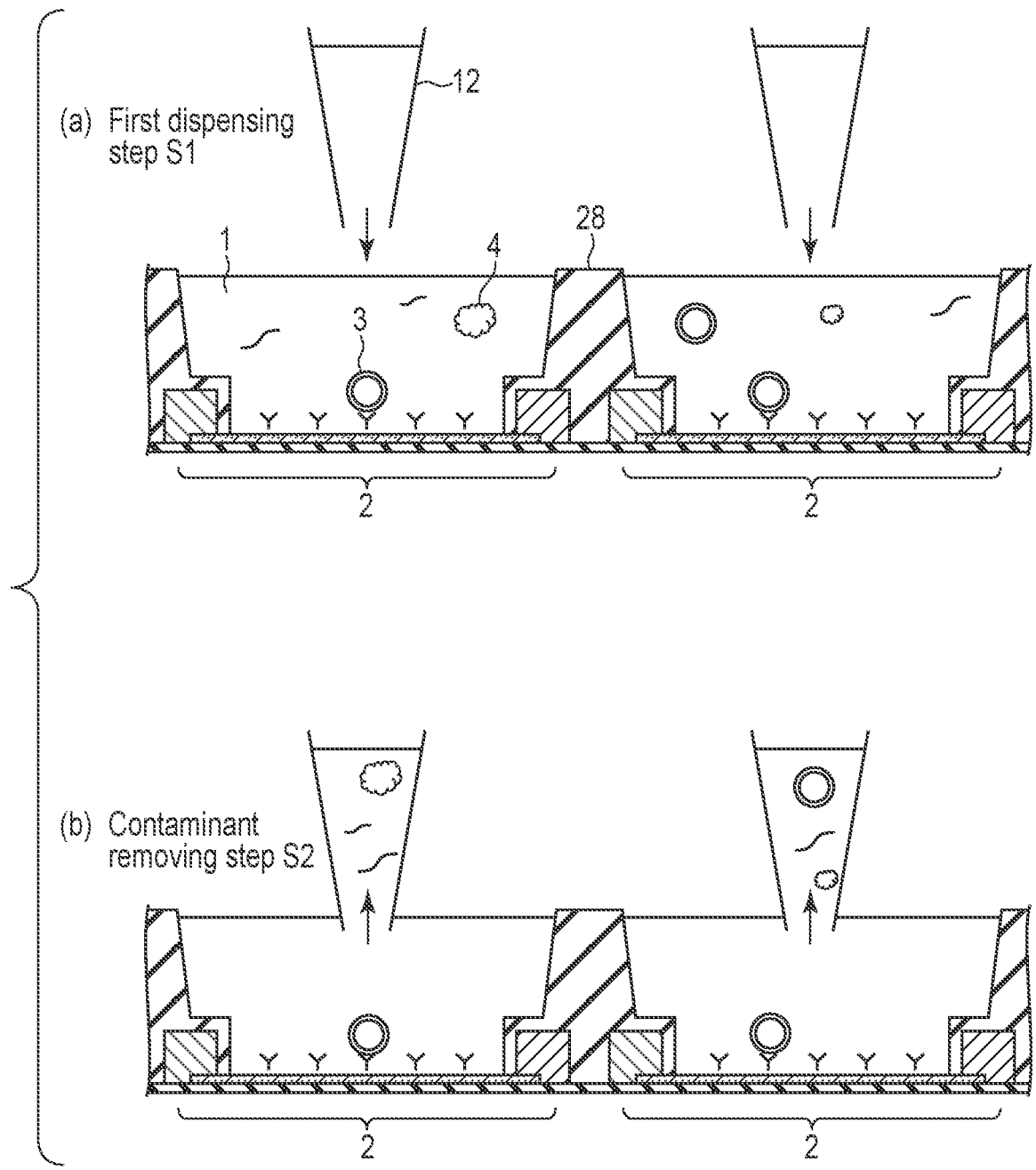
FIG. 14 is a diagram illustrating an example of a procedure of the analysis method of the embodiment.

FIG. 14 illustrates a case where the partition wall 28 of the first container 2 is higher than a liquid level of the specimen 1. In this example, the specimen 1 is isolated for each of the first containers 2 from the beginning. The first dispensing step S1 can be performed using a micropipette 12 as illustrated in part (a) of FIG. 14. At this time, it is preferable that the first container 2 is not provided with a lid, and the humidity around the first container 2 is maintained high. As illustrated in part (b) of FIG. 14, the contaminant removing step S2 can be performed by repeating a plurality of times of capturing the target particle 3 on the bottom surface, sucking out the specimen 1 using the micropipette 12, and substituting the specimen 1 with a new solvent. At this time, if a column for adsorbing contaminants 4 is disposed inside the micropipette 12, the contaminants 4 can be more efficiently removed.

Thereafter, as illustrated in parts (c) to (e) of FIG. 15, addition of the probe 100 (probe adding step S3), removal of the excessive probe 100*a* (probe removing step S4), addition of the cleavage reagent 6 as necessary (reporter portion separation), and collection of the reporter portion 103 can also be performed using the micropipette 12.

Although one micropipette 12 may be used, each step can be performed simply in a short time by using a plurality of micropipettes 12 prepared for each first container 2. In particular, when the reporter portion 103 and the amplification product thereof are collected, it is preferable to use a plurality of micropipettes 12 in order to prevent contamination.

FIG. 16 illustrates a case where the partition wall 28 of the first container 2 is lower than a liquid level of the specimen 1. In this example, the first dispensing step S1 can be performed by pouring the specimen 1 onto the plurality of first containers 2 at a time as illustrated in part (a) of FIG. 16. As illustrated in part (b) of FIG. 16, the contaminant removing step S2 can be performed by capturing the target particle 3 on the bottom surface, then pouring a new solvent 13 onto the plurality of first containers 2 at a time, and draining the specimen 1 containing the contaminants 4. Thereafter, the addition of the probe 100 (probe adding step S3) and the removal of the excessive probe 100 (probe removing step S4) may be performed in this state; however, before the first amplifying step S5 at the latest, or in a case where the reporter portion 103 is separated, before the separation, the solvent 13 is drained until the water surface of the solvent 13 comes below the partition wall 28 as illustrated in part (c) of FIG. 16, and the liquid is isolated for each first container 2. Subsequent steps can be performed in the same manner as in FIG. 15. In this case, the dispensing of the specimen 1, the removal of the contaminants 4, the addition of the probe 100, and the removal of the excessive probe 100 can be performed at a time, which is preferable.

FIG. 17 illustrates a case where there is no partition wall 28 of the first container 2. In this example, similarly to FIG. 16, the first dispensing step S1 is performed by pouring the specimen 1 onto the first container 2 at a time, and after the target particle 3 is captured on the bottom surface, the contaminant removing step S2 can be performed by pouring an appropriate solvent 13 onto the first container 2 and draining the specimen 1 containing the contaminants 4. Thereafter, the addition of the probe 100 (probe adding step S3) and the removal of the excessive probe 100 (probe removing step S4) may be performed in this state; however, before the first amplifying step S5 at the latest, or in a case where the reporter portion 103 is separated, before the separation, the partition wall 28 is installed so as to be pressed from above as illustrated in part (c) of FIG. 17, and the liquid is isolated for each first container 2. Subsequent steps can be performed in the same manner as in FIG. 15. In this case, the dispensing of the specimen 1, the removal of the contaminants 4, the addition of the probe 100, and the removal of the excessive probe 100 can be performed at a time, which is preferable. In addition, since the partition wall 28 is installed after the contaminants 4 are cleaned and removed, the contaminants 4 do not adhere. Therefore, there is no risk that the contaminants 4 remaining in the partition wall 28 are re-mixed.

The addition and collection of the specimen 1 or the reagent into the first container 2 may be performed using a microchannel instead of a pipette.

(Method including Step of Collecting Target Particle 3)

In a further embodiment, as illustrated in FIG. 18, the analysis method may further include a target particle collecting step S10 of collecting the target particle 3 from each first container 2 after the analyzing step S9.

Figure 19:
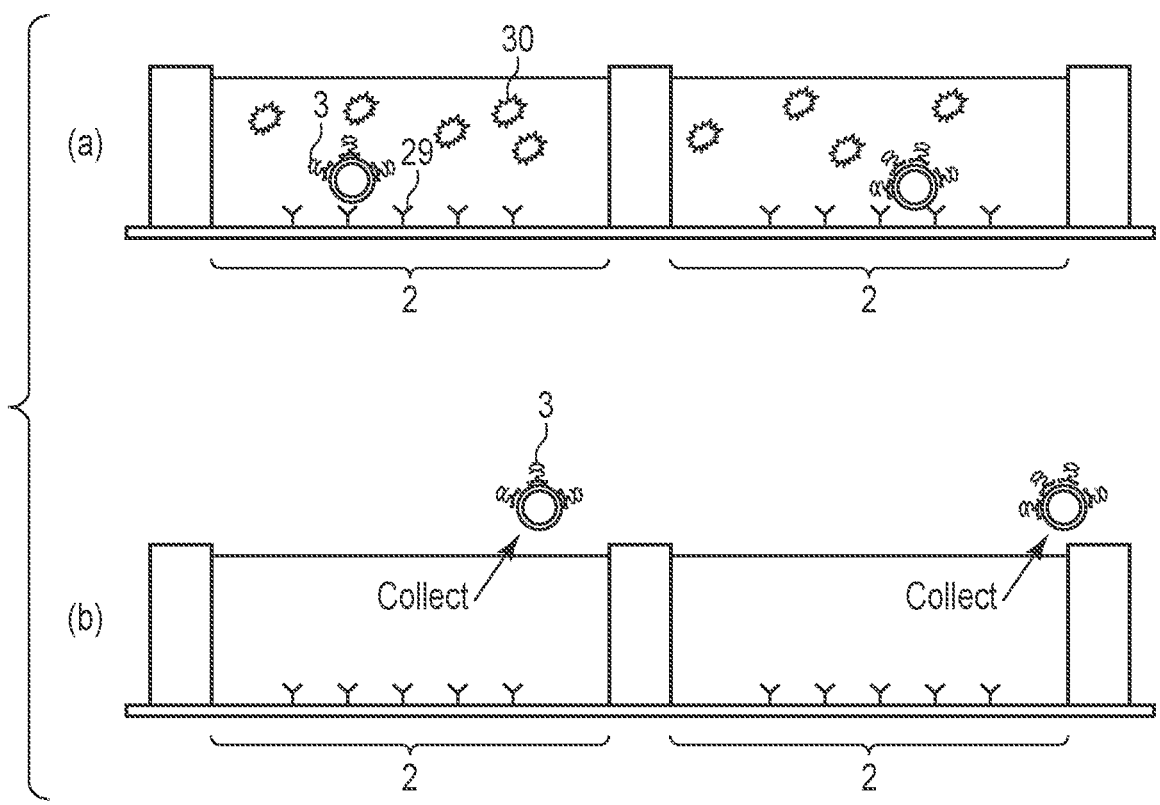
FIG. 19 is a diagram illustrating an example of a procedure of collecting a target particle in the analysis method of the embodiment.

In this step, first, the target particle 3 is desorbed from each of the first containers 2. When the capturing body 29 is used, a desorption reagent 30 is added as illustrated in part (a) of FIG. 19. The desorption reagent 30 is a reagent that separates the capturing body 29 from the target particle 3, separates the capturing body from the first container 2, or decomposes the capturing body 29. For example, in a case of being fixed by using a Tim4 protein, the desorption reagent 30 is a chelating agent. Next, as illustrated in part (b) of FIG. 19, the target particle 3 is collected. When dielectrophoresis is used, the application of a voltage to the electrode may be stopped, and the target particle 3 may be collected. When the magnetic beads 10 are used, the magnetism may be released to collect the magnetic beads 10. After the collected magnetic beads 10 are magnetically concentrated, a desorption reagent for desorbing the target particles 3 from the magnetic beads 10 is added to desorb the target particles 3, and the target particles 3 are collected.

The recovered target particles 3 are homogenized as necessary, and can be used for further analysis, for example, genome analysis, proteome analysis, metabolome analysis, or the like.

In the present method, when the reporter portion 103 is separated, the target particle 3 may be damaged by a method in which the reporter portion 103 is liberated by heating or adjusting the salt concentration, and thus it is preferable to perform the separation by a method in which the cleavage portion 102 is cleaved with the cleavage reagent 6.

In addition, it is preferable that the first amplifying step S5 is not performed in the first container 2 and is performed by collecting the reporter portion 103 in another container. This is because when the first amplifying step S5 is performed in the first container 2, it may be necessary to raise the temperature of the first container 2 to a high temperature, which may destroy the target particle 3.

In one embodiment, step from S1 to S10 may be continuously carried out without performing another step between any of these steps.

Analytical Reagent

According to an embodiment, an analytical reagent for a target particle used in the present analysis method is provided. The reagent includes first to m-th probes 100.

The analytical reagent may further include a cleavage reagent 6, a common primer set corresponding to the first to m-th probes 100, first to m-th specific primer sets, an amplification reagent and/or a desorption reagent 30 as necessary.

Analyzer

Figure 20:
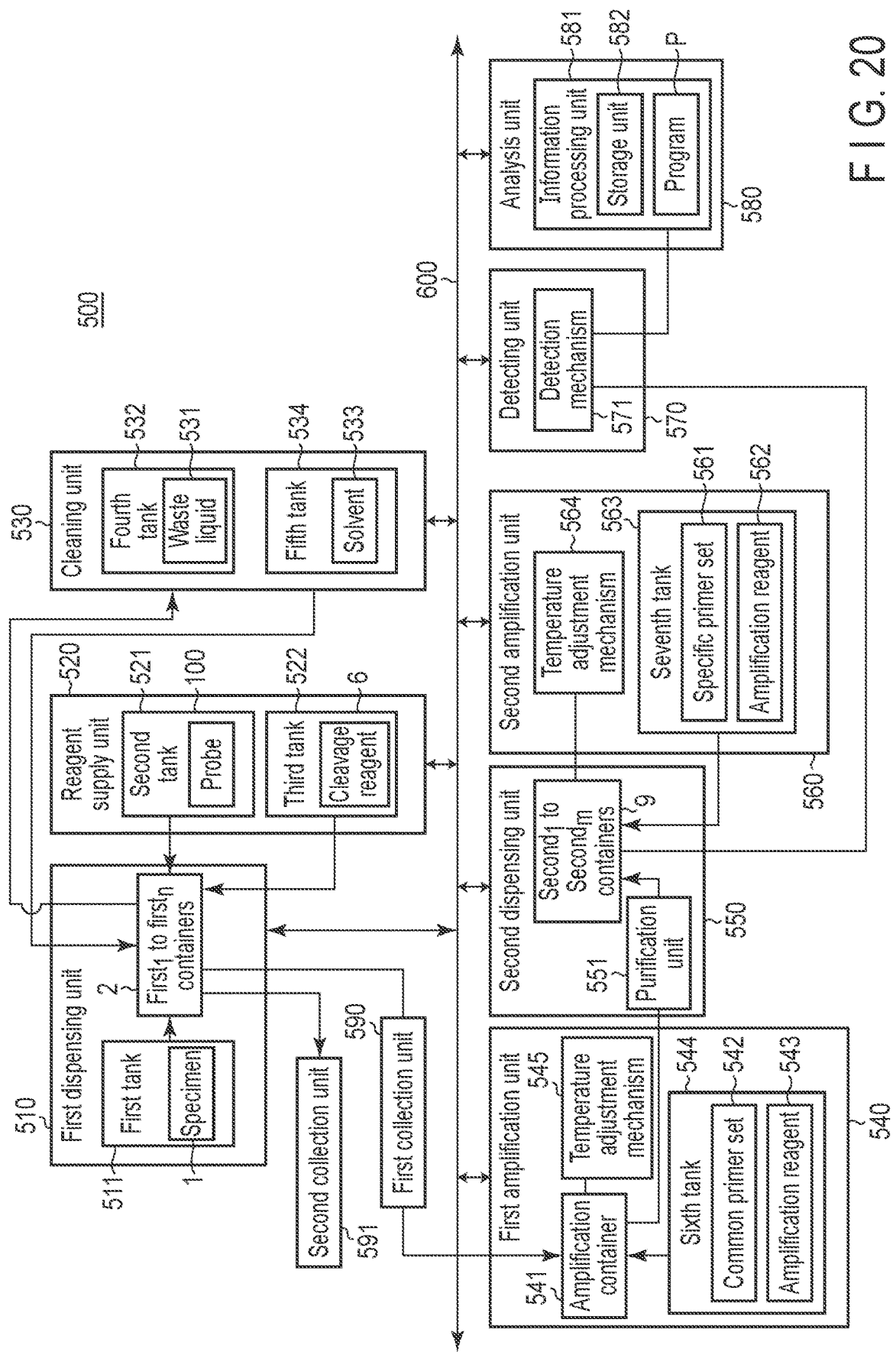
FIG. 20 is a block diagram illustrating an example of an analyzer according to the embodiment.

According to an embodiment, an analyzer for a target particle used in the present analysis method is provided. As illustrated in FIG. 20, an analyzer 500 may include a first dispensing unit 510 that dispenses a specimen 1 into $first_1$ to $first_n$ containers 2, a reagent supply unit 520 that supplies a probe 100 (a cleavage reagent as necessary) to the $first_1$ to $first_n$ containers 2, a cleaning unit 530 that removes contaminants or excessive probes from the $first_1$ to $first_n$ containers 2, a first amplification unit 540 that amplifies a reporter portion 103, a second dispensing unit 550 that dispenses an amplification product into $second_1$ to $second_m$ containers 9, a second amplification unit 560 that amplifies the amplification product using a specific primer set, a detecting unit 570 that detects the amplification product by the specific primer set in the $second_1$ to $second_m$ containers 9, and an analysis unit 580 that analyzes a target particle from a detection result in the detecting unit. The thick arrows in FIG. 20 indicate the transfer of a substance between units by a pipette or a channel.

The first dispensing unit 510 includes, for example, the $first_1$ to $first_n$ container 2, a first tank 511 that stores the specimen 1, and n pipettes or n channels (not illustrated) that supply the specimen from the first tank to the $first_1$ to $first_n$ container 2. The pipette is movable and includes a pump, for example, and moves onto the first tank 511 to suck the specimen 1 and moves onto the $first_1$ to $first_n$ container 2 to discharge the specimen into the $first_1$ to $first_n$ container 2. The n channels include, for example, a pump and connect the first tank 511 and the $first_1$ to $first_n$ container 2. The first tank 511 may further include a mechanism for adding a solvent in order to dilute the specimen 1 to a desired concentration.

The reagent supply unit 520 includes, for example, a second tank 521 that accommodates the probe 100, a third tank 522 that accommodates the cleavage reagent 6 as necessary, and n pipettes or n channels (not illustrated) that supply the probe 100 or the cleavage reagent 6 from the second tank 521 or the third tank 522 to the $first_1$ to $first_n$ container 2, respectively.

The cleaning unit 530 includes, for example, a fourth tank 532 for accommodating a waste liquid 531, a fifth tank 534 for accommodating a solvent 533, n pipettes or n channels (not illustrated) for sending the waste liquid 531 from the $first_1$ to $first_n$ containers 2 to the fourth tank 532, and n pipettes or n channels (not illustrated) for supplying the solvent 533 from the fifth tank 534 to the $first_1$ to $first_n$ containers 2.

The first amplification unit 540 includes n amplification containers 541 for accommodating the reporter portion group 7, a sixth tank 544 for accommodating a common primer set 542 and an amplification reagent 543, and n pipettes or n channels (not illustrated) for supplying the reagent from the sixth tank 544 to the n amplification containers 541. The first amplification unit 540 further includes a temperature adjustment mechanism 545, and adjusts the internal temperature of the amplification container 541 to a temperature suitable for the amplification conditions. Although not illustrated, when the first amplifying step is performed in the $second_1$ to $second_m$ containers 9 without collecting the reporter portion, the $first_1$ to $first_n$ containers 2 include a temperature adjustment mechanism, and the reagent is supplied from the sixth tank 544 to the $first_1$ to $first_n$ containers 2.

The second dispensing unit 550 includes the $second_1$ to $second_m$ containers 9 and n to n×m pipettes or n×m channels (not illustrated) for supplying a specimen from each of the n amplification containers to the $second_1$ to $second_m$ containers 9. Although not illustrated, when the first amplifying step is performed in the $second_1$ to $second_m$ containers 9 without collecting the reporter portion 103, there are provided n to n×m pipettes or n×m channels for dispensing the amplification product from the $first_1$ to $first_n$ containers 2 into the $second_1$ to $second_m$ containers 9. Further, there is also provided a purification unit 551 having a function of washing and removing the common primer set in the specimen when the specimen is supplied from each of the n amplification containers to the $first_1$ to $first_n$ containers 9. Specifically, a nucleic acid adsorption purification column such as Diffinity RapidTip (registered trademark) manufactured by Merc, Inc., is used for the n to n×m pipettes, or a similar nucleic acid adsorption purification column is provided in the middle of the n×m channels.

The second amplification unit 560 includes a seventh tank 563 that accommodates the first to m-th specific primer sets 561 and the amplification reagent 562, a pipette or a channel (not illustrated) that supplies the reagent from the seventh tank 563 to the $second_1$ to $second_m$ containers 9, and a temperature adjustment mechanism 564 that adjusts the temperature of the $second_1$ to $second_m$ containers 9.

The detecting unit 570 includes, for example, a detection mechanism 571 that detects the presence or absence of an amplification product in the $second_1$ to $second_m$ containers 9. The detection mechanism 571 may be a known mechanism that generally detects an amplification product of nucleic acid, and includes, for example, a fluorescence detection device, an absorptiometer, an electrode, or the like. These may be provided in the $second_1$ to $second_m$ containers 9, or may be provided, for example, in another container, and the amplification product may be transferred thereto to perform detection. Further, the detection mechanism 571 may also be provided in the amplification container 541 of a first amplification unit. In a case where the detection mechanism 571 is provided in the amplification container 541 of the first amplification unit, it is possible to know whether or not the nucleic acid including the reporter portion group 7 is contained in the amplification container 541 of the first amplification unit, that is, whether or not the target particle is present in the $first_1$ to $first_n$ containers 2 of the first dispensing unit before performing the steps after the second dispensing unit.

The analysis unit 580 includes an information processing unit 581. For example, the information processing unit 581 determines the type of the target surface marker contained in each of the first containers 2 from the detection result obtained by the detecting unit 570, determines the type of the target particles 3 contained in the first container 2 therefrom, and analyzes the composition of all the target particles 3 or the target surface marker in the specimen 1. Furthermore, the analysis unit 580 may determine the health condition of the subject from which the specimen 1 is collected, for example, the presence or absence of a disease, using the composition information of the target particle 3 or the target surface marker. The information processing unit 581 may include a storage unit 582 that stores experimental results and calculation formulas used for these determinations and analyses, and a program P for controlling the determinations and analyses and the operations of the respective units.

The analyzer 500 may further include a first collection unit 590 that individually collects the reporter portion from the $first_1$ to $first_n$ containers 2 and sends the reporter portion to the amplification container 541 of the first amplification unit 540. The first collection unit includes n pipettes or n channels for sending collected products from the $first_1$ to $first_n$ containers 2 to the amplification container.

The analyzer 500 may further include a further second collection unit 591 that desorbs and collects the target particles 3 from the $first_1$ to $first_n$ containers 2, a further analysis unit that provides the collected target particles 3 for further analysis, an input unit that inputs a parameter, and/or a display unit that displays an analysis result. The above units are electrically connected to each other via, for example, a bus 600.

According to the present analyzer 500, the type, amount, concentration, and the like of the plurality of target particles 3 contained in the specimen 1 can be comprehensively analyzed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for analyzing a target particle in a specimen, the method comprising:
   a) dispensing the specimen into $first_1$ to $first_n$ containers configured to capture the target particle;
   b) removing a contaminant from the specimen, the contaminant being other than the target particle to be captured;
   c) cladding first to m-th probes to each container of the $first_1$ to $first_n$ containers, each of the first to m-th probes having at least a binding portion and a nucleic acid reporter portion,
      the binding portion of each of the first to m-th probes respectively binding to first to m-th surface markers of the target particle;
      the nucleic acid reporter portion of each of the first to m-th probes respectively including a common amplification sequence to which a common primer set binds and a specific amplification sequence to which a specific primer set binds disposed in a region amplified by the common amplification sequence;

d) removing excessive probes of the first to m-th probes that have not bound to the target particle;

e) individually amplifying the reporter portion for each of the $first_1$ to $first_n$ containers using the common primer set to obtain first to n-th amplification products;

f) removing an excessive common primer set from the first to n-th amplification products;

g) dispensing the first to n-th amplification products into respective $second_1$ to $second_m$ containers;

h) further amplifying the first to n-th amplification products in the $second_1$ to $second_m$ containers using the first to m-th specific primer sets, respectively; and i) analyzing at least one of a presence, absence or type of the target particles captured in the $first_1$ to $first_n$ containers by determining the types of surface markers present in the $first_1$ to $first_n$ containers based on the presence or absence of the first to n-th amplification products by the first to m-th specific primer sets in the $second_1$ to $second_m$ containers, wherein n and m are integers of 2 or more.

2. The method according to claim 1, wherein the $first_1$ to $first_n$ containers include a sensor capable of detecting target particles contained in the $first_1$ to $first_n$ containers, and the method further comprises detecting the number of the target particles contained in the $first_1$ to $first_n$ containers.

3. The method according to claim 2, wherein the $first_1$ to $first_n$ containers at least include:
   a first electrode and a second electrode disposed at an interval at a bottom;
   a channel in which the first electrode is electrically connected to one end and the second electrode is connected to the other end, and
   an insulator covering the first electrode and the second electrode,
   wherein the target particle is detected by detecting a change in a value of a current flowing between the first electrode and the second electrode due to capture of the target particle on the channel.

4. The method according to claim 3, wherein the channel is a graphene nanoribbon or a carbon nanotube.

5. The method according to claim 1, wherein in each of the $first_1$ to $first_n$ containers comprises a capturing mechanism configured to capture the target particles, the capturing mechanism comprising at least one of:
   a capturing body fixed to an inner surface of the $first_1$ to $first_n$ containers,
   a dielectrophoresis device that guides the target particles to bottoms of the $first_1$ to $first_n$ containers, or
   an electrophoresis device that guides the target particles to bottoms of the $first_1$ to $first_n$ containers.

6. The method according to claim 1, wherein the binding portion is an antibody or an antigen-binding fragment, a lectin, a naturally occurring nucleic acid, an artificial nucleic acid, an aptamer, a peptide aptamer, an oligopeptide, or a protein.

7. The method according to claim 1, further comprising:
   after step d) and prior to step e), performing a step d2) of separating the reporter portion from the first to m-th probes that have bound to target particles.

8. The method according to claim 7, wherein the first to m-th probes include a cleavage portion between the binding portion and the reporter portion, and the reporter portion is separated by adding a cleavage reagent that cleaves the cleavage portion to the $first_n$ to $first_n$ containers.

9. The method according to claim 8, wherein the cleavage reagent is a Cas9 protein and a guide RNA, and the cleavage portion has a target sequence of the guide RNA and a protospacer adjacent motif (PAM) sequence;
   the cleavage reagent is an endonuclease, and the cleavage portion has a target sequence of the endonuclease;
   the cleavage reagent is imidazole, and the cleavage portion has His-Tag; or
   the cleavage reagent is a reducing agent, and the cleavage portion has a disulfide bond.

10. The method according to claim 1, wherein the reporter portion is a double-stranded nucleic acid.

11. The method according to claim 10, wherein the separation of the reporter portion is performed by denaturing the reporter portion to release a strand not linked to the binding portion of the reporter portion.

12. The method according to claim 7, further comprising:
   after step d2), collecting the reporter portion from each of the $first_1$ to $first_n$ containers into separate containers, and
   individually performing amplification using the common primer set in each of the separate containers.

13. The method according to claim 1, further comprising desorbing the target particle from the $first_1$ to $first_n$ containers and collecting the target particle after step i).

14. The method according to claim 1, wherein step b) further comprises:
   adding magnetic beads to the specimen, the magnetic beads configured to bind to the target particle,
   fixing the magnetic beads to a magnetism generator; and
   removing the contaminants by substituting a solution comprising the contaminants with a second solution while the magnetic beads are fixed to the magnetism generator.

15. The method according to claim 14, wherein the magnetic beads are added such that a concentration of the added magnetic beads is higher than a concentration of the target particle in the specimen.

16. The method according to claim 1, wherein the target particle is a virus or an extracellular target particle.

17. The method according to claim 1, further comprising:
   prior to step a), diluting the specimen to a concentration lower than a concentration at which two target particles are contained in the $first_1$ to $first_n$ containers.

18. The method according to claim 14, further comprising:
   prior to step a), diluting the specimen to a concentration lower than a concentration at which two target particles are contained in the $first_1$ to $first_n$ containers.

* * * * *

UNITED STATES PATENT AND TRADEMARK OFFICE
CERTIFICATE OF CORRECTION

PATENT NO. : 11,834,700 B2
APPLICATION NO. : 17/447469
DATED : December 5, 2023
INVENTOR(S) : Yoshiaki Sugizaki Page 1 of 1

It is certified that error appears in the above-identified patent and that said Letters Patent is hereby corrected as shown below:

In the Claims

Claim 1, Column 20, Line 57, "cladding" should read as --adding--.

Claim 8, Column 22, Line 9, "$first_n$ to $first_n$" should read as --$first_1$ to $first_n$--.

Signed and Sealed this
Twenty-eighth Day of May, 2024

Katherine Kelly Vidal
*Director of the United States Patent and Trademark Office*